(12) United States Patent
Labaudiniere et al.

(10) Patent No.: US 9,249,112 B2
(45) Date of Patent: Feb. 2, 2016

(54) SOLID FORMS OF A TRANSTHYRETIN DISSOCIATION INHIBITOR

(75) Inventors: Richard Frederic Labaudiniere, Medfield, MA (US); Michael Henry O'Neill, Painesville, OH (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 14/345,111

(22) PCT Filed: Sep. 12, 2012

(86) PCT No.: PCT/IB2012/054748
§ 371 (c)(1),
(2), (4) Date: Mar. 14, 2014

(87) PCT Pub. No.: WO2013/038351
PCT Pub. Date: Mar. 21, 2013

(65) Prior Publication Data
US 2015/0031735 A1    Jan. 29, 2015

Related U.S. Application Data

(60) Provisional application No. 61/535,551, filed on Sep. 16, 2011.

(51) Int. Cl.
| C07D 498/00 | (2006.01) |
| C07D 263/57 | (2006.01) |
| C07H 5/06 | (2006.01) |

(52) U.S. Cl.
CPC .............. *C07D 263/57* (2013.01); *C07H 5/06* (2013.01)

(58) Field of Classification Search
CPC .. C07D 263/57; C07D 277/66; C07D 235/18; C07D 249/20; C08K 5/35
USPC ........................................................ 548/224
See application file for complete search history.

(56) References Cited

U.S. PATENT DOCUMENTS

| 3,551,433 A | 12/1970 | Hydro et al. |
| 3,551,443 A | 12/1970 | Duennenberger et al. |
| 4,025,636 A | 5/1977 | Dunwell et al. |
| 4,025,637 A | 5/1977 | Dunwell et al. |
| RE29,608 E | 4/1978 | Evans et al. |
| 4,107,169 A | 8/1978 | Schrage |
| 4,416,892 A | 11/1983 | Dawson |
| 5,037,842 A | 8/1991 | Goldstein |
| 5,200,420 A | 4/1993 | Goldmann et al. |
| 5,254,692 A | 10/1993 | Goldmann et al. |
| 5,354,759 A | 10/1994 | Oku et al. |
| 5,412,099 A | 5/1995 | Goldmann et al. |
| 5,441,946 A | 8/1995 | Pauls et al. |
| 5,552,426 A | 9/1996 | Lunn et al. |
| 5,563,128 A | 10/1996 | Pauls et al. |
| 5,714,496 A | 2/1998 | Brown et al. |
| 5,837,390 A | 11/1998 | Kishii et al. |
| 6,107,491 A | 8/2000 | Eldin |
| 6,277,853 B1 | 8/2001 | Perez et al. |
| 6,420,418 B1 | 7/2002 | Hagmann et al. |
| 6,495,568 B1 | 12/2002 | Dack et al. |
| 6,544,989 B2 | 4/2003 | Mathews et al. |
| 6,589,953 B2 | 7/2003 | Perez et al. |
| 6,602,619 B2 | 8/2003 | Lin et al. |
| 6,623,930 B2 | 9/2003 | Kerwin et al. |
| 6,689,887 B2 | 2/2004 | Kerwin et al. |
| 6,693,098 B2 | 2/2004 | Cournoyer et al. |
| 6,794,403 B2 | 9/2004 | Malamas et al. |
| 7,214,695 B2 * | 5/2007 | Kelly ................... C07D 263/57 514/375 |
| 7,214,696 B2 | 5/2007 | Kelly et al. |
| 7,560,488 B2 | 7/2009 | Kelly et al. |
| 8,168,663 B2 | 5/2012 | Kelly et al. |
| 8,653,119 B2 | 2/2014 | Kelly et al. |
| 2001/0056100 A1 | 12/2001 | Cournoyer et al. |
| 2002/0049142 A1 | 4/2002 | Mathews et al. |
| 2002/0061891 A1 | 5/2002 | Perez et al. |
| 2002/0107258 A1 | 8/2002 | Kerwin et al. |
| 2003/0040525 A1 | 2/2003 | Kerwin et al. |
| 2003/0129448 A1 | 7/2003 | Lin et al. |
| 2003/0199562 A1 | 10/2003 | Malamas et al. |
| 2003/0220367 A1 | 11/2003 | Cournoyer et al. |
| 2003/0232877 A1 | 12/2003 | Sikorski et al. |
| 2004/0006056 A1 | 1/2004 | Harris et al. |
| 2004/0029933 A1 | 2/2004 | Zhao et al. |
| 2004/4048858 | 3/2004 | Sikorski et al. |
| 2004/0102435 A1 | 5/2004 | Barlaam et al. |
| 2004/0152140 A1 | 8/2004 | Kelly et al. |

(Continued)

FOREIGN PATENT DOCUMENTS

| DE | 602336 | 8/1934 |
| DE | 2314238 | 9/1973 |

(Continued)

OTHER PUBLICATIONS

Ratner, M. "Spotlight focuses on protein-folding therapies". Oct. 2009. Nature Biotechnology 27(10). p. 874.*

(Continued)

*Primary Examiner* — Nyeemah A Grazier
*Assistant Examiner* — Sagar Patel

(57) ABSTRACT

The present invention relates to solid forms of the N-methyl-D-glucamine (meglumine) salt of 6-carboxy-2-(3,5-dichlorophenyl)-benzoxazole and to methods for their preparation. The invention is also directed to pharmaceutical compositions containing at least one solid form and to the therapeutic or prophylactic use of such solid forms and compositions.

9 Claims, 18 Drawing Sheets

(56) References Cited

U.S. PATENT DOCUMENTS

| | | |
|---|---|---|
| 2004/0209776 A1 | 10/2004 | Farooq et al. |
| 2004/0229894 A1 | 11/2004 | Kerwin et al. |
| 2005/0090472 A1 | 4/2005 | Yoshida et al. |
| 2005/0282780 A1 | 12/2005 | Labaudiniere |
| 2010/0120919 A1 | 5/2010 | Kelly et al. |

FOREIGN PATENT DOCUMENTS

| | | |
|---|---|---|
| DE | 4208535 | 9/1992 |
| DE | 4304650 | 8/1994 |
| EP | 0479161 | 4/1992 |
| EP | 0611660 | 8/1994 |
| WO | 98/27972 | 7/1998 |
| WO | 00/78733 | 12/2000 |
| WO | 01/12183 | 2/2001 |
| WO | 01/14354 | 3/2001 |
| WO | 01/27088 | 4/2001 |
| WO | 01/74786 | 10/2001 |
| WO | 02/16333 | 2/2002 |
| WO | 02/46168 | 6/2002 |
| WO | 02/051821 | 7/2002 |
| WO | 03/020698 | 3/2003 |
| WO | 03/045930 | 6/2003 |
| WO | 2004/046123 | 6/2003 |
| WO | 03/074516 | 9/2003 |
| WO | 03/089418 | 10/2003 |
| WO | 2004/064771 | 8/2004 |
| WO | 2004/083189 | 9/2004 |
| WO | 2004/083195 | 9/2004 |
| WO | 2004/084824 | 10/2004 |
| WO | 2004/092140 | 10/2004 |
| WO | 2004/094395 | 11/2004 |
| WO | 2004/098494 | 11/2004 |
| WO | 2011/116123 | 9/2011 |
| WO | 2013/166041 | 11/2013 |
| WO | 2013/168014 | 11/2013 |

OTHER PUBLICATIONS

Kolstoe, S. E., P. Mangione, V. Bellotti, G.W. Taylor, G.A. Tennent, S. Deroo, A.J. Morrison, A.J.A. Cobb, A. Coyne, M.G. McCammon, T.D. Warner, J. Mitchell, R. Gill, M.D. Smith, S.V. Ley, C.V. Robinson, S.P. Wood, and M.B. Pepys. "Trap. of palind. ligands within native TTR prevents amyloid form.". Nov. 23, 2010. PNAS 107(47). pp. 20483-20488.*

Almeida et al., "Small Transthyretin (TTR) Ligands as Possible Therapeutic Agents in TTR Amyloidoses," Curro Drug Targets CNS Nerolog. Disord., 4(5): 587-96 (2005).

Anderson, et al., "Tools for Purifying the Product: Column Chromatography, Crystallization and Reslurrying", Practical Process Research and Development, Academic Press, pp. 223-247 (2000).

Aydin et al., "Analgesic and Antispasmodic Activities of 2-(2-Nitrophenyl)-1 H-benzimidazole 5-Carboxylic Acid: Evidence for the Importance of the 2-(o-Substituted Phenyl) Group", Pharmazie 58:405-408 (2003).

Baures et al., "Discovering Transthyretion Amyloid Fibril Inhibitors by Limited Screening", Bioorganic & Medicinal Chemistry 6:1389-1401 (1998).

Baures et al., "Synthesis and Evaluation of Inhibitors of Transthyretin Amyloid Formation Based on the Non-Steroidal Anti-Inflammatory Drug, Flufenamic Acid", Bioorganic & Medicinal Chemistry 7:1339-1347 (1999).

Beaulieu et al., "Non-Nucleoside Inhibitors of the Hepatitis C Virus NS5B Polymerase: Discovery and Preliminary SAR of Benzimidazole Derivatives", Bioorganic and Medicinal Chemistry Letters 14: 119-124 (2004).

Byrn, S, et al., "Pharmaceutical Solids: A Strategic Approach to Regulatory Considerations", Pharmaceutical Research, Kluwer Academic Pulishers, vol. 12, No. 7:945-954 (1995).

Caira, "Crystallin Polymorphism of Organic Compounds", Topics in Current Chemistry, vol. 198, 163-208, (1998).

Chen, et al., J. Pharmaceutical and Biomedical Ananlysis, 26:63 (2001).

Denny et al., "Structure-Activity Relationship for the Mutagenic Activity of Tricyclic Intercalating Agents in *Salmonella typhimurium*," Mutation Research 232(2): 233-241 (1990).

Editorial, "Orphan Amyloid Diseases", Nature Structural Biology 7(4):259-260 (2000).

Essassi and Fifani, "Synthese et Heterocyclization des (Pyrazolyl-3(5))-2-Benzimidazoles en Catalyse par Transfert de Phase", Bull Soc Chim Belg 96(1 ):63-67 (1987).

Ferrer, N.; Nogues-Carulla, J.M., Diamonds and Related Materials, 5:598-602 (1996).

Goker and Tebrizli, "Synthesis of 1,2-Disubstituted Benzimidazole-9(6)-Carboxamides and Evaluation of Their Antimicrobial Activity", II Farmaco 51 (1 ):53-58 (1996).

Goker et al., "Synthesis and Antimicrobial Activity of Some New 2-Phenyl-N-Substituted Carboxamido-1H-Benzimidazole Derivatives", Arch Pharm Med Chem 334:148-152 (2001).

Green et al., "Synthesis and Characterization of Potent Bivalent Amyloidosis Inhibitors That Bind Prior to Transthyretin Tetramerization", J Am Chem Soc 125:13404-13414 (2003).

Hammarstrom et al., "Prevention of Transthyretin Amyloid Disease by Changing Protein Misfolding Energetics", Science 299:713-716 (2003).

Hammarstrom et al., "Trans-Suppression of Misfolding in an Amyloid Disease", Science 293:2459-2462 (2001).

Hari et al., "Extending the Scope of Chromium-Manganese Redox-Coupled Reactions: A One-Pot Synthesis of Benzoxazoles," J. Org. Chem. 66: 991-996 (2001).

Harwood, et al., "Experimental organic chemistry—Principles and practice", Experimental Chemistry—Organic Chemistry and Reaction, 127-132, (1989).

Haskell et al., "Neuraminidase Inhibition and Viral Chemotherapy", Journal of Medicinal Chemistry 13(4):697-704 (1970).

Hillard et al., Multiple Mechanisms of Action for Inhibitors of Histidine Protein Kinases from Bacterial Two-Component Systems, Antimicrobial Agents and Chemotherapy 43(7): 1693-1699 (1999).

Hizano and Yabuta, "Synthesis of Organosulfur Compounds. VIII. Cyclization Products from the Modified Willgerodt-Kindler Reaction", Chem Pharm Bull 21 (3):511-517 (1973).

Jennings et al., "Efficient Synthesis of (±)-seco-Cyclopropaneindoline Analogs of CC-1 065", Heterocyclic Communication 7(1) (2001).

Kelly, "The Environment Dependency of Protein Folding Best Explains Prion and Amyloid Diseases", PNAS 95:930-932 (1998).

Kim et al., "Structure-Activity Relationships of Benzimidazoles and Related Heterocycles as, ~it Topoisomerase I Poisons", Bioorganic and Medicinal Chemistry 4(4 ):621-630 (1996).

Klabunde et al., "Rational Design of Potent Human Transthyretin Amyloid Disease Inhibitors", Nature Structural Biology 7(4 ):31321 (2000).

Kolstoe, et al., "Trapping of palindromic ligands within native transthyretin prevents amyloid formation", Proceedings of the National Academy of Science, vol. 107, No. 47:20483-20488, (2010).

Kreimeyer et al., "Sumarin Analogues with a 2-Phenylbenzimidazole Moiety as Partial Structure", Pharmazie 52(4 ):268-271 (1997).

Lashuel, et al., "New Class of inhibitors of Amyloid-beta Fibril Formation", J. Biol. Chem. 277(45):42881-42890 (2002).

Lee et al., "Solid-Phase Combinatorial Synthesis of Benzothiazole and 2,3-Dihydro-[1 ,5]-Benzothiazepine Derivatives", Tetrahedron Letters 42:109-111 (2001).

Lin et al., "Bioisosteric Replacement of Anilide with Benzoxazole: Potent and Orally Bioavailable Antagonists of VLA-4", Bioorganic & Medicinal Chem Letters 14:2331-2334 (2004).

Magy et. aL., A Transthyretin Mutation (Tyr78Phe) Associated with Peripheral Neuropathy, Carpal Tunnel Syndrome, and Skin Amyloidosis, Amyloid, 10(1): 29-33 (2003).

Miller, "The Misfolding Diseases Unfold," Beremans, Ltd., pp. 1-4 (2004).

Miroy et al., "Inhibiting Transthyretion Amyloid Fibril Inhibitors via Protein Stabilization", PNAS USA 93:15051-15056 (1996).

(56) References Cited

OTHER PUBLICATIONS

Oza et al., "Synthesis and Evaluation of Anthranilic Acid-Based Trabsthyretin Amyloid Fibril Inhibitors", Bioorganic & Medicinal Chem Letters 9:1-6 (1999).

Oza et al., "Synthesis, Structure and Activity of Diclofenac Analogues as Transthyretin Amyloid Fibril Formation Inhibitors", J Med Chem 45:321-332 (2002).

Peterson, et al., "Inhibiting Transthyretin Conformational Changes That Leat to Amyuloid Fibril Formation", PNAS 95:12956-12960 (1998).

Petrassi et al., "Structure-Based Design of N-Phenyl Phenoxazine Transthyretion Amyloid Fibril Inhibitors", J Am Chem Soc 122(10):2178-2192 (2000).

Purkey et al., "Evaluating the Binding Selectivity of Transthyretion Amyloid Fibril Inhibitors in Blood Plasma", PNAS USA 98(10):5566-5571 (2001).

Ratner, "Spotlight focuses on protein-misfolding therapies", Nature Biotechnology, vol. 27, No. 10, Oct. 1, 2009, p. 874.

Razavi et al., "Benzoxazoles as Transthyretion Amyloid Fibril Inhibitors: Synthesis, Evaluation, and Mechanism of Action", Angew Chem 115:2864-2867 ((2003).

Razavi et al., "Benzoxazoles as Transthyretion Amyloid Fibril Inhibitors: Synthesis, Evaluation, and Mechanism of Action", Angew Chem Int Ed. 42:2758-2761 (2003).

Robinson et al., "Lessons from the AN 1792 Alzheimer Vaccine: Lest We Forget," Neurobiology of Aging 25: 609-615 (2004).

Rtishchev et al., "Absorption and Luminescence in the Series of 2-Phenylbenzothiazole and Related Compounds", Russian Journal of General Chemistry 63(2):303-309 (1993).

Sacchettini and Kelly, "Therapeutic Strategies for Human Amyloid Diseases", Nature Reviews 1 :267-275 (2002).

Sekijima et al., "Orally administered diflunisal stabilizes transthyretin against dissociation required for amyloidogenesis" Amyloid 13(4): 236-249 (2006).

Shimizu et al., "A Case of Biopsy-Proven Leptomeningeal Amyloidosis and Intravenous Ig-Responsive Polyneuropathy Associated with the Ala25Thr Transthyretin Gene Mutation," Amyloid, 13(1): 37-41 (2006).

Singh et al., "Synthetic Utility of Catalytic Fe(III)/Fe(II) Redox Cycling Towards Fused Heterocycles: a Facile Acces to Substituted Benzimidazole, Bis-Benzimidazole and Imidazopyridine Derivatives", Synthesis 10:1380-1390 (2000).

Stedman, "Stedman's Medical Dictionary," 27th ed., Lippincott Williams & Wilkins, p. 65 (2000).

Stephens and Bower, The Preparation of Benziminazoles and Benzoxazoles from Schiff's Bases, Part II, J Chem Soc (UK) 1722-1726 (1950).

Thongnopkun, P.; Ekgasit, S., Diamonds and Related Materials, 14:1592-1599 (2005).

Tojo et al., "Diflunisal stabilizes familial amyloid polyneuropathy-associated transthyretin variant tetramers in serum against dissociation required for amyloidogenesis", Neuroscience Research 56:441-449 (2006).

Xue et al., "Design, Synthesis and in Vitro Activities of a Series of Benzimidazole/Benzoxazole Glycoprotein lib/lila Inhibitors", Bioorganic & Medicinal Chem Letters 6(3):339-344 (1996).

Yazaki et al., "A New Transthyretin Variant Leu55Gln in a Patient With Systemic Amyloidosis," Amyloid 9(4): 268-71 (2002).

Coelho, T. et al. "Long-term effects of tafamidis for the treatment of transthyretin familial amyloid polyneuropathy" Journal of Neurology 260:11, 2802-2814 (2013).

Coelho, T. et al. "Tafamidis for transthyretin familial amyloid polyneuropathy: A randomized, controlled trial" Neurology 79:8, 785-792 (2012).

Johnson, S. M. et al. "The Transtyretin Amyloidoses: From Delineating the Molecular Mechanism of Aggregation Linked to Pathology to Regulatory-Agency-Approved Drug" Journal of Molecular Biology 421:2-3, 185-203 (2012).

Bulawa, C. E. et al. "Tafamidis, a potent and selective transtyretin kinetic stabilizer that inhibits the amyloid cascade" PNAS 109:24, 9629-9634 (2012).

Yamamoto, T. et al. "Nickel-Catalyzed C-H Arylation of Azoles with Haloarenes: Scope, Mechanism, and Applications to the Synthesis of Bioactive Molecules" Chemistry—A European Journal 17:36, 10113-10122 (2011).

\* cited by examiner

| Angle (°2-Theta) | Relative Intensity (≥10%) |
|---|---|
| 5.9 | 10 |
| 10.7 | 16 |
| 11.8 | 55 |
| 12.1 | 13 |
| 13.3 | 72 |
| 14.8 | 12 |
| 16.7 | 10 |
| 17.9 | 67 |
| 18.8 | 49 |
| 19.0 | 51 |
| 19.9 | 13 |
| 21.4 | 60 |
| 21.7 | 100 |
| 23.4 | 31 |
| 25.4 | 29 |
| 26.1 | 29 |
| 26.6 | 32 |
| 27.6 | 48 |

| Angle (°2-Theta) | Relative Intensity (≥10%) |
|---|---|
| 28.1 | 15 |
| 29.5 | 10 |
| 29.9 | 32 |
| 30.5 | 10 |
| 31.1 | 22 |
| 31.8 | 12 |
| 32.1 | 16 |
| 33.1 | 12 |
| 33.5 | 14 |
| 35.1 | 20 |
| 36.2 | 14 |
| 36.6 | 14 |
| 38.0 | 10 |
| 38.2 | 12 |
| 38.4 | 13 |
| 39.6 | 13 |

FIG. 4B

| Peak (cm-1) | Relative Intensity |
|---|---|
| 3076 | M |
| 3067 | W |
| 3041 | W |
| 3021 | W |
| 3012 | W |
| 2967 | W |
| 2923 | W |
| 1625 | S |
| 1616 | S |
| 1596 | S |
| 1574 | M |
| 1548 | S |
| 1522 | W |
| 1483 | W |
| 1464 | W |
| 1438 | W |
| 1428 | M |
| 1418 | M |
| 1410 | M |
| 1395 | W |
| 1383 | M |
| 1368 | M |
| 1344 | W |
| 1307 | M |
| 1274 | S |
| 1232 | S |
| 1201 | W |
| 1174 | W |
| 1138 | W |
| 1126 | W |
| 1094 | W |
| 1079 | W |
| 1056 | W |
| 1013 | W |
| 995 | M |
| 984 | W |

| Peak (cm-1) | Relative Intensity |
|---|---|
| 959 | W |
| 949 | W |
| 943 | W |
| 887 | W |
| 873 | W |
| 845 | W |
| 815 | W |
| 794 | W |
| 758 | W |
| 729 | W |
| 685 | W |
| 604 | W |
| 588 | W |
| 494 | W |
| 446 | W |
| 429 | W |
| 412 | W |
| 387 | W |
| 353 | W |
| 328 | W |
| 287 | W |
| 262 | W |
| 234 | M |
| 220 | W |
| 175 | W |
| 129 | W |
| 115 | W |

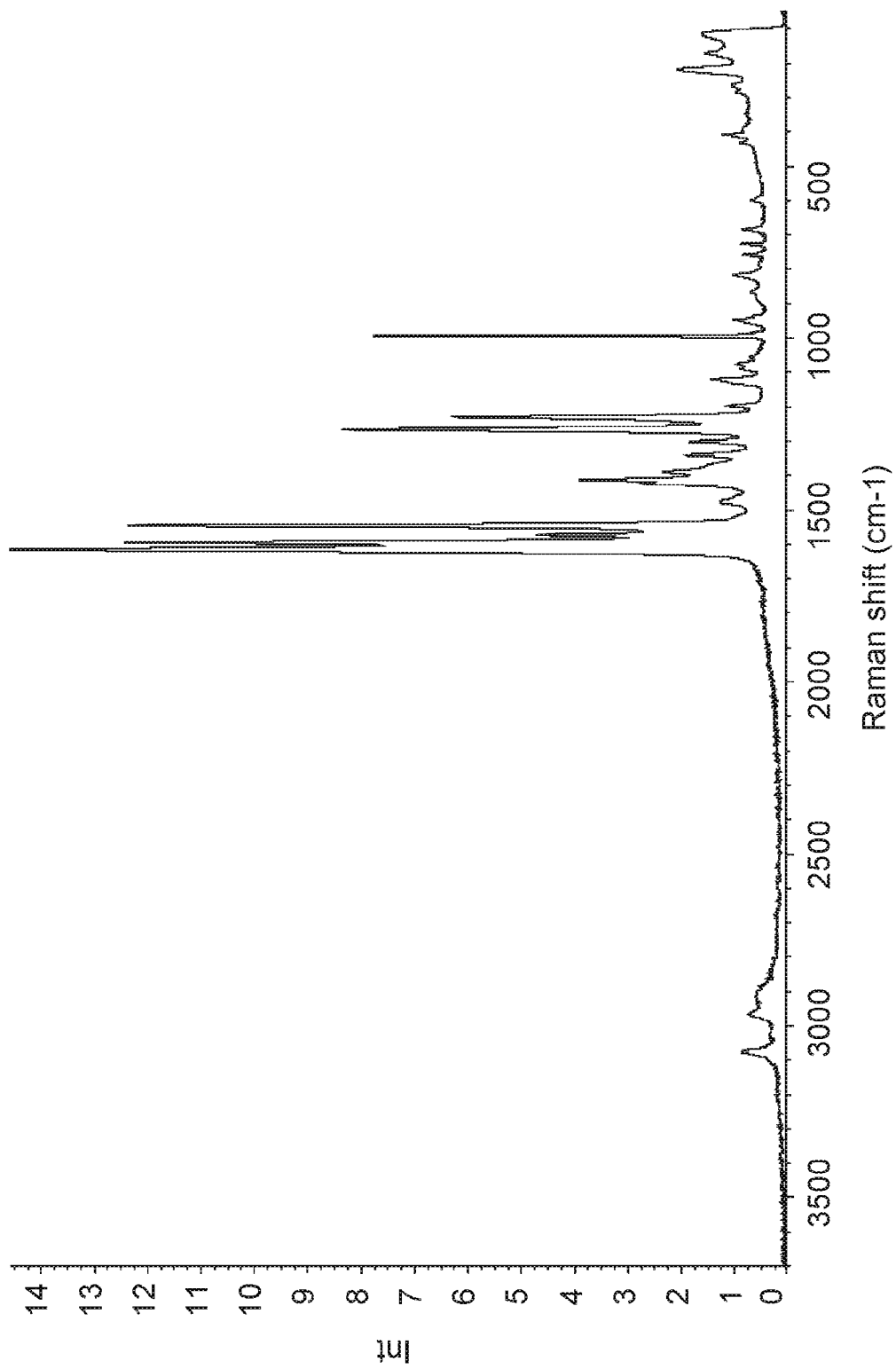

FIG. 5B

| Peak (cm-1) | Relative Intensity |
|---|---|
| 3074 | W |
| 3024 | W |
| 2968 | W |
| 2914 | W |
| 1614 | S |
| 1595 | S |
| 1573 | M |
| 1545 | S |
| 1477 | W |
| 1424 | M |
| 1413 | M |
| 1390 | M |
| 1372 | M |
| 1340 | M |
| 1301 | M |
| 1265 | S |
| 1230 | M |
| 1198 | W |
| 1120 | M |
| 1089 | W |
| 1075 | W |
| 1054 | W |
| 994 | S |
| 984 | W |
| 946 | W |
| 936 | W |
| 867 | W |
| 816 | W |
| 785 | W |
| 758 | W |
| 726 | W |
| 685 | W |
| 598 | W |
| 432 | W |
| 409 | W |
| 348 | W |

| Peak (cm-1) | Relative Intensity |
|---|---|
| 286 | W |
| 265 | W |
| 218 | M |
| 170 | M |
| 115 | M |

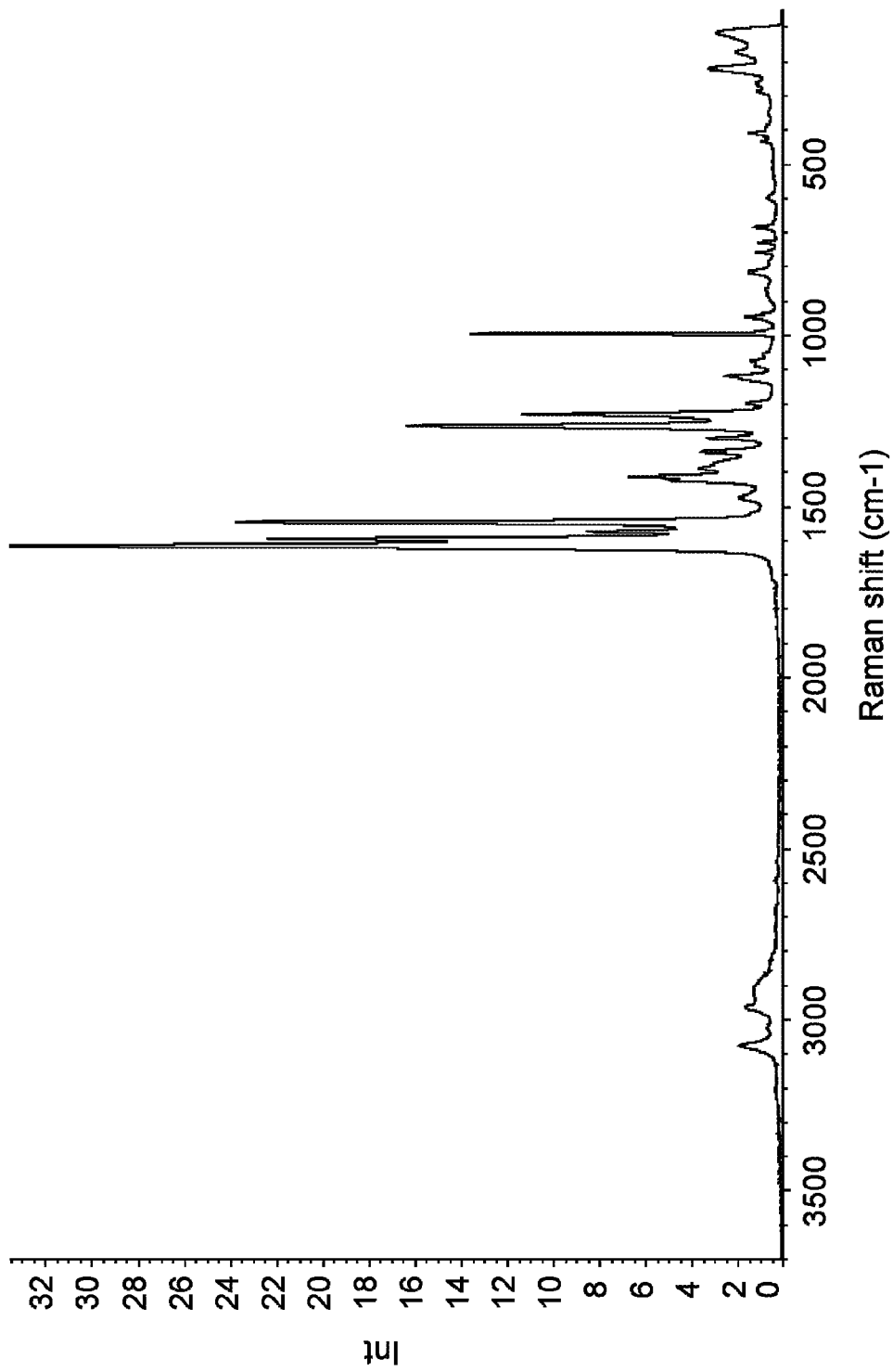

FIG. 6B

| Peak (cm⁻¹) | Relative Intensity |
|---|---|
| 3075 | W |
| 3029 | W |
| 2964 | W |
| 2912 | W |
| 1615 | S |
| 1594 | S |
| 1573 | M |
| 1546 | S |
| 1474 | W |
| 1423 | M |
| 1412 | M |
| 1390 | M |
| 1374 | W |
| 1339 | M |
| 1300 | M |
| 1264 | M |
| 1230 | M |
| 1198 | W |
| 1119 | W |
| 1087 | W |
| 1075 | W |
| 1056 | W |
| 995 | M |
| 984 | W |
| 946 | W |
| 935 | W |
| 867 | W |
| 814 | W |
| 789 | W |
| 757 | W |
| 728 | W |
| 684 | W |
| 600 | W |
| 431 | W |
| 409 | W |
| 350 | W |

| Peak (cm⁻¹) | Relative Intensity |
|---|---|
| 287 | W |
| 264 | W |
| 220 | M |
| 172 | W |
| 115 | W |

FIG. 7B

| Peak (cm-1) | Relative Intensity |
|---|---|
| 3418 | W |
| 3328 | W |
| 3131 | W |
| 3075 | W |
| 3066 | W |
| 2966 | W |
| 2930 | W |
| 2914 | W |
| 2828 | W |
| 2660 | W |
| 2467 | W |
| 1620 | W |
| 1599 | W |
| 1581 | W |
| 1570 | W |
| 1547 | W |
| 1479 | W |
| 1474 | W |
| 1459 | W |
| 1440 | W |
| 1420 | W |
| 1410 | W |
| 1380 | M |
| 1367 | M |
| 1342 | M |
| 1336 | M |
| 1305 | M |
| 1273 | M |
| 1254 | W |
| 1241 | W |
| 1219 | W |
| 1201 | W |
| 1172 | W |
| 1154 | W |
| 1137 | W |
| 1125 | W |

| Peak (cm-1) | Relative Intensity |
|---|---|
| 1108 | W |
| 1077 | M |
| 1046 | W |
| 1032 | W |
| 1010 | S |
| 974 | W |
| 964 | W |
| 958 | W |
| 950 | W |
| 943 | W |
| 906 | W |
| 886 | W |
| 873 | M |
| 855 | W |
| 835 | W |
| 814 | S |
| 802 | M |
| 781 | S |
| 758 | W |
| 749 | W |
| 728 | S |
| 709 | M |
| 683 | M |
| 666 | S |
| 593 | S |
| 564 | M |
| 559 | W |
| 542 | W |

FIG. 8B

| Peak (cm$^{-1}$) | Relative Intensity |
|---|---|
| 3205 | M |
| 3075 | M |
| 2932 | W |
| 2840 | W |
| 1615 | W |
| 1595 | W |
| 1547 | S |
| 1471 | W |
| 1438 | W |
| 1411 | W |
| 1379 | S |
| 1339 | S |
| 1298 | M |
| 1264 | M |
| 1240 | M |
| 1198 | W |
| 1171 | W |
| 1127 | W |
| 1079 | S |
| 1038 | S |
| 946 | W |
| 936 | W |
| 885 | W |
| 861 | S |
| 806 | S |
| 780 | S |
| 745 | S |
| 725 | S |
| 684 | S |
| 664 | S |
| 632 | S |

FIG. 9B

| Peak (cm⁻¹) | Relative Intensity |
|---|---|
| 3189 | M |
| 3074 | M |
| 2924 | W |
| 2838 | W |
| 1615 | W |
| 1596 | W |
| 1547 | S |
| 1471 | W |
| 1437 | M |
| 1410 | M |
| 1364 | S |
| 1338 | S |
| 1297 | S |
| 1262 | S |
| 1239 | M |
| 1198 | M |
| 1172 | W |
| 1126 | W |
| 1118 | W |
| 1077 | S |
| 1035 | S |
| 945 | M |
| 935 | M |
| 885 | M |
| 862 | S |
| 802 | S |
| 783 | S |
| 747 | S |
| 725 | S |
| 682 | S |
| 664 | S |

| 13C Chemical Shifts [ppm] |
| --- |
| 34.9 |
| 60.2 |
| 66.3 |
| 68.0 |
| 73.9 |
| 74.7 |
| 76.8 |
| 112.6 |
| 119.0 |
| 124.6 |
| 125.1 |
| 126.6 |
| 127.7 |
| 132.1 |
| 133.9 |
| 137.5 |
| 142.0 |
| 149.6 |
| 160.6 |
| 171.5 |

| 13C Chemical Shifts [ppm] |
| --- |
| 35.1 |
| 52.5 |
| 72.0 |
| 111.5 |
| 118.5 |
| 125.2 |
| 127.3 |
| 131.1 |
| 136.3 |
| 141.7 |
| 149.1 |
| 159.9 |
| 173.5 |

| 13C Chemical Shifts [ppm] |
| --- |
| 34.9 |
| 53.7 |
| 71.6 |
| 111.9 |
| 119.4 |
| 126.1 |
| 135.4 |
| 143.4 |
| 150.0 |
| 161.0 |
| 173.1 |

…

SOLID FORMS OF A TRANSTHYRETIN DISSOCIATION INHIBITOR

CROSS REFERENCE TO RELATED APPLICATIONS

This application is a 371 national phase filing of International Patent Application No. PCT/IB2012/054748, filed on Sep. 12, 2012, which claims the benefit under 35 U.S.C. § 119 to U.S. Provisional Patent Application serial number 61/535,551, filed on Sep. 16, 2011, the disclosures of which are hereby incorporated by reference.

FIELD OF THE INVENTION

The present invention relates to solid forms of the N-methyl-D-glucamine (meglumine) salt of 6-carboxy-2-(3,5-dichlorophenyl)-benzoxazole and to methods for their preparation. The invention is also directed to pharmaceutical compositions containing at least one solid form and to the therapeutic or prophylactic use of such solid forms and compositions.

BACKGROUND OF THE INVENTION

This invention relates to solid forms of 6-carboxy-2-(3,5-dichlorophenyl)-benzoxazole meglumine (also referred to as "Compound 1") that are useful in the treatment of transthyretin amyloid diseases, such as senile systemic amyloidosis (SSA), familial amyloid polyneuropathy (FAP) and familial amyloid cardiomyopathy (FAC), in mammals. This invention also relates to compositions including such solid forms, and to methods of using such compositions in the treatment of transthyretin amyloid disease in mammals, especially humans.

Carboxy-2-phenyl-benzoxazoles, such as 6-carboxy-2-(3,5-dichlorophenyl)-benzoxazole, and their salts, are described in U.S. Pat. Nos. 7,214,695 and 7,214,696; and in U.S. Patent Application Publication No. 2010/0120919 (all of which are hereby incorporated by reference in their entireties). Methods of making carboxy-2-phenyl-benzoxazoles, as well as pharmaceutical compositions comprising the same, are also described therein.

Compound 1 stabilizes the protein transthyretin (TTR), dissociation of which is implicated in TTR amyloidosis (i.e., Compound 1 prevents dissociation of the native TTR tetramer into monomers, which results in the inhibition of TTR amyloid fibril formation) and is being developed for use in the treatment of transthyretin amyloid diseases.

Solid forms are of interest to the pharmaceutical industry and especially to those involved in the development of suitable dosage forms. If the solid form is not held constant during clinical or stability studies, the exact dosage form used or studied may not be comparable from one lot to another. It is also desirable to have processes for producing a compound with the selected solid form in high purity when the compound is used in clinical studies or commercial products since impurities present may produce undesired toxicological effects. Certain solid forms may also exhibit enhanced thermodynamic stability or may be more readily manufactured in high purity in large quantities, and thus are more suitable for inclusion in pharmaceutical formulations. Certain solid forms may display other advantageous physical properties such as lack of hygroscopic tendencies, filterability, improved solubility, and enhanced rates of dissolution due to different lattice energies.

The discussion of the background to the invention herein is included to explain the context of the present invention. This is not to be taken as an admission that any of the material referred to was published, known, or part of the common general knowledge in any country as of the priority date of any of the claims.

SUMMARY OF THE INVENTION

Although multiple solid forms of Compound 1 have been identified, each solid form can be uniquely identified by several different analytical parameters, alone or in combination, such as, but not limited to: powder X-ray diffraction pattern peaks or combinations of two or more peaks; solid state NMR $^{13}C$ chemical shifts or combinations of two or more chemical shifts; Raman shift peaks or combinations of two or more Raman shift peaks; and Infrared shift peaks or combinations of two or more infrared shift peaks or combinations thereof.

One aspect of the present invention provides a crystalline form of 6-carboxy-2-(3,5-dichlorophenyl)-benzoxazole meglumine, represented as Compound 1, wherein said crystalline form has a powder X-ray diffraction pattern comprising peaks at diffraction angles (2θ) of 10.7±0.2, 11.8±0.2, and 13.3±0.2. In another embodiment, the crystalline form of Compound 1 has a powder X-ray diffraction pattern comprising peaks at diffraction angles (2θ) of 10.7±0.2, 11.8±0.2, 13.3±0.2, and 14.8±0.2. In another embodiment, the crystalline form of Compound 1 has a powder X-ray diffraction pattern comprising peaks at diffraction angles (2θ) of 10.7±0.2, 11.8±0.2, 13.3±0.2, 14.8±0.2 and 21.7±0.2.

Another aspect of the present invention provides a crystalline form of Compound 1, wherein said crystalline form has a powder X-ray diffraction pattern comprising peaks at diffraction angles (2θ) essentially the same as shown in FIG. 1A.

Another aspect of the present invention provides a liquid crystalline form of Compound 1, wherein said liquid crystalline form has a powder X-ray diffraction peak position essentially the same as shown in FIG. 2A. Another aspect of the present invention provides a liquid crystalline form of Compound 1, wherein said liquid crystalline form has a powder X-ray diffraction peak position essentially the same as shown in FIG. 2B.

Another aspect of the present invention provides an amorphous form of Compound 1, wherein said amorphous form has a powder X-ray diffraction peak position essentially the same as shown in FIG. 3A. Another aspect of the present invention provides an amorphous form of Compound 1, wherein said amorphous form has a powder X-ray diffraction peak position essentially the same as shown in FIG. 3B.

Another aspect of the present invention provides a crystalline form of Compound 1, wherein said crystalline form has a Raman spectrum comprising Raman shift peaks ($cm^{-1}$) at 1625±2, 1596±2, and 1548±2. In another embodiment, the crystalline form of Compound 1 has a Raman spectrum comprising Raman shift peaks ($cm^{-1}$) at 1625±2, 1616±2, 1596±2, and 1548±2. In another embodiment, the crystalline form of Compound 1 has a Raman spectrum comprising Raman shift peaks ($cm^{-1}$) at 1625±2, 1616±2, 1596±2, 1574±2 and 1548±2.

Another aspect of the present invention provides a crystalline form of Compound 1, wherein said crystalline form has a Raman spectrum comprising Raman shift peaks ($cm^{-1}$) at positions essentially the same as shown in FIG. 4A.

Another aspect of the present invention provides a liquid crystalline form of Compound 1, wherein said liquid crystalline form has a Raman spectrum comprising Raman shift peaks ($cm^{-1}$) at positions essentially the same as shown in FIG. 5A.

Another aspect of the present invention provides an amorphous form of Compound 1, wherein said amorphous form has a Raman spectrum comprising Raman shift peaks ($cm^{-1}$) at positions essentially the same as shown in FIG. 6A.

Another aspect of the present invention provides a crystalline form of Compound 1, wherein said crystalline form has an infrared spectrum comprising infrared shift peaks ($cm^{-1}$) at 1581±2, 1273±2, 1010±2, 906±2 and 873±2.

Another aspect of the present invention provides a crystalline form of Compound 1, wherein said crystalline form has an infrared spectrum comprising infrared shift peaks ($cm^{-1}$) essentially the same as shown in FIG. 7A.

Another aspect of the present invention provides a liquid crystalline form of Compound 1, wherein said liquid crystalline form has an infrared spectrum comprising infrared shift peaks ($cm^{-1}$) at 1547±2, 1264±2, 936±2, 861±2, and 632±2.

Another aspect of the present invention provides a liquid crystalline form of Compound 1, wherein said liquid crystalline form has an infrared spectrum comprising infrared shift peaks ($cm^{-1}$) essentially the same as shown in FIG. 8A.

Another aspect of the present invention provides an amorphous form of Compound 1, wherein said amorphous form has an infrared spectrum comprising infrared shift peaks ($cm^{-1}$) at 1547±2, 1262±2, 935±2, 862±2 and 802±2.

Another aspect of the present invention provides an amorphous form of Compound 1, wherein said amorphous form has an infrared spectrum comprising infrared shift peaks ($cm^{-1}$) essentially the same as shown in FIG. 9A.

Another aspect of the present invention provides a crystalline form of Compound 1, wherein said crystalline form has a solid state NMR spectrum comprising $^{13}C$ chemical shifts (ppm) at 112.6±0.2, 133.9±0.2, and 171.5±0.2.

Another aspect of the present invention provides a crystalline form of Compound 1, wherein said crystalline form has a solid state NMR spectrum comprising $^{13}C$ chemical shifts at positions essentially the same as shown in FIG. 10A.

Another aspect of the present invention provides a liquid crystalline form of Compound 1, wherein said liquid crystalline form has a solid state NMR spectrum comprising $^{13}C$ chemical shifts (ppm) at 118.5±0.5, 136.3±0.5, and 159.9±0.5.

Another aspect of the present invention provides a liquid crystalline form of Compound 1, wherein said liquid crystalline form has a solid state NMR spectrum comprising $^{13}C$ chemical shifts at positions essentially the same as shown in FIG. 11A.

Another aspect of the present invention provides an amorphous form of Compound 1, wherein said amorphous form has a solid state NMR spectrum comprising $^{13}C$ chemical shifts (ppm) at 135.4±0.5, 143.4±0.5, and 161.0±0.5.

Another aspect of the present invention provides an amorphous form of Compound 1, wherein said amorphous form has a solid state NMR spectrum comprising $^{13}C$ chemical shifts at positions essentially the same as shown in FIG. 12A.

Another aspect of the present invention provides a crystalline form of Compound 1, wherein said crystalline form has a Raman spectrum comprising a Raman shift peak ($cm^{-1}$) at 1625 cm±2; and a solid state NMR spectrum comprising a $^{13}C$ chemical shift (ppm) at 133.9±0.2.

Another aspect of the present invention provides a crystalline form of Compound 1, wherein said crystalline form has a Raman spectrum comprising a Raman shift peak ($cm^{-1}$) at 1625 cm±2; and a solid state NMR spectrum comprising a $^{13}C$ chemical shift (ppm) at 171.5±0.2.

Another aspect of the present invention provides a liquid crystalline form of Compound 1, wherein said crystalline form has a Raman spectrum comprising a Raman shift peak ($cm^{-1}$) at 1573 cm±2; and a solid state NMR spectrum comprising a $^{13}C$ chemical shift (ppm) at 136.3±0.2.

Another aspect of the present invention provides an amorphous form of Compound 1, wherein said crystalline form has a Raman spectrum comprising a Raman shift peak ($cm^{-1}$) at 1573 cm±2; and a solid state NMR spectrum comprising a $^{13}C$ chemical shift (ppm) at 143.4±0.2.

In certain embodiments, the present invention relates to any of the above-referenced crystalline forms of Compound 1, wherein said form is non-hygroscopic and anhydrous.

In certain embodiments, the present invention relates to any of the above-referenced crystalline forms of Compound 1, wherein said form comprises a plurality of small crystallites of Compound 1.

In certain embodiments, the present invention relates to any of the above-referenced crystalline forms of Compound 1, wherein said form comprises a plurality of needle shaped crystals of Compound 1.

In a further aspect, the present invention contemplates that any one of the solid forms of Compound 1 as described herein can exist in the presence of the any other of the solid forms or mixtures thereof. Accordingly, in one embodiment, the present invention provides the crystalline form, the liquid crystalline form or the amorphous form of Compound 1 as described herein, wherein said crystalline, liquid crystalline or amorphous form is present in a solid form that includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of Compound 1. For example, in one embodiment is a solid form of Compound 1 comprising a crystalline form of Compound 1 that has any one of the powder X-ray diffraction patterns, Raman spectra, IR spectra and/or NMR spectra described above, wherein said solid form includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of Compound 1.

In certain embodiments, the present invention relates to any of the above-referenced forms of Compound 1, wherein said form is substantially pure (i.e., a substantially pure crystalline form, a substantially pure liquid crystalline form, or a substantially pure amorphous form).

A further aspect of the present invention provides a pharmaceutical composition comprising the crystalline, liquid crystalline or amorphous forms of Compound 1 as described herein. In a further aspect, the invention provides an oral dosage form comprising the crystalline, liquid crystalline or amorphous forms of Compound 1 or pharmaceutical compositions described herein. For example, in one embodiment the oral dosage form is a tablet, pill or capsule. For example, in one embodiment, the oral dosage form is a tablet or capsule.

In one embodiment the invention provides a tablet comprising any of the solid forms of Compound 1 or pharmaceutical compositions described herein. For example, in one embodiment the tablet comprises from about 1 to about 10 mg of the crystalline form of Compound 1. Further, for example, the tablet comprises from about 1 to about 5 mg of the crystalline form of Compound 1. Even further, for example, the tablet comprises about 1 mg of the crystalline form of Compound 1. Even further, for example, the tablet comprises about 2 mg, about 3 mg, about 4 mg, or about 5 mg of the crystalline form of Compound 1.

In one embodiment the invention provides a soft gelatin capsule comprising any of the solid forms of Compound 1 or pharmaceutical compositions described herein. For example, in one embodiment the soft gelatin capsule comprises from about 1 to about 10 mg of the crystalline form of Compound 1. Further, for example, the soft gelatin capsule comprises from about 1 to about 5 mg of the crystalline form of Compound 1. Even further, for example, the soft gelatin capsule comprises about 1 mg of the crystalline form of Compound 1. Even further, for example, the soft gelatin capsule comprises about 2 mg, about 3 mg, about 4 mg, or about 5 mg of the crystalline form of Compound 1.

A further aspect of the present invention provides a method for preparing Compound 1 in crystalline form, said method comprising heating 6-carboxy-2-(3,5-dichlorophenyl)-benzoxazole and adding a solution of N-methyl-D-glucamine in water dropwise. For example, in one embodiment, said heating is carried out in the presence of an appropriate solvent. In one embodiment, the solvent comprises 2-propanol and water.

A further aspect of the present invention provides a method for preparing Compound 1 in liquid crystalline form, said method comprising dissolving crystalline Compound 1 in water, freezing the resulting solution and freeze drying the resulting frozen solution.

A further aspect of the presents invention provides a method for preparing Compound 1 in amorphous form, said method comprising heating crystalline Compound 1 in a container until it melts and then placing the container in liquid nitrogen. For example, in one embodiment, said container is an aluminum pan and said heating is carried out on a hot plate at 200° C.

A further aspect of the present invention provides a method of treating transthyretin amyloid diseases, such as senile systemic amyloidosis (SSA), familial amyloid polyneuropathy (FAP) and familial amyloid cardiomyopathy (FAC), in a mammal, the method comprising administering to the mammal a therapeutically effective amount of any of the solid forms of Compound 1 or any of the pharmaceutical compositions described herein. In certain embodiments, the solid form administered is the crystalline form. In certain embodiments, the solid form administered is the liquid crystalline form. In certain embodiments, the solid form administered is the amorphous form.

BRIEF DESCRIPTION OF THE DRAWINGS

FIG. 5 depicts (a) a Raman spectrum of liquid crystalline Compound 1 carried out on a Nicolet NXR FT-Raman spectrometer equipped with a 1064 nm Nd:YVO$_4$ laser and a liquid cooled Germanium detector and (b) a corresponding peak list.

FIG. 6 depicts (a) a Raman spectrum of amorphous Compound 1 carried out on a Nicolet NXR FT-Raman spectrometer equipped with a 1064 nm Nd:YVO$_4$ laser and a liquid cooled Germanium detector and (b) a corresponding peak list.

DETAILED DESCRIPTION OF THE INVENTION

Figures 1A, 1B:
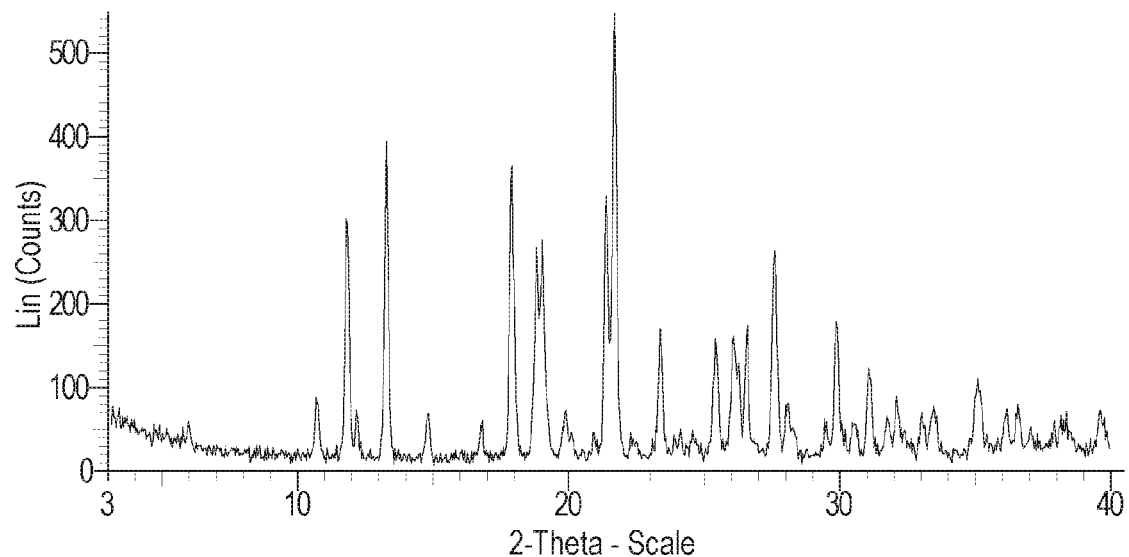
FIG. 1 depicts (a) a XRPD pattern of crystalline Compound 1 carried out on a Bruker D8 diffractometer and (b) a corresponding peak list.

It has been found that Compound 1 can exist in a crystalline form, a two-dimensionally ordered liquid crystalline form or an amorphous form. These forms may be used in a formulated product for the treatment of transthyretin amyloid diseases. Each form may have advantages over the others in terms of properties such as bioavailability, stability, and manufacturability. In one aspect of the invention, a crystalline form of Compound 1 has been discovered which is likely to be more suitable for bulk preparation and handling than the liquid crystalline or amorphous forms. Processes for producing the crystalline form of Compound 1 in high purity are described herein. Another object of the present invention is to provide a process for the preparation of each solid form of Compound 1, substantially free from other solid forms of Compound 1. Additionally it is an object of the present invention to provide pharmaceutical formulations comprising Compound 1 in different solid forms as discussed above, and methods of treating transthyretin amyloid diseases by administering such pharmaceutical formulations.

Definitions

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of "treating" as defined immediately above.

As used herein, transthyretin or TTR is a 55 kDa homotetramer characterized by 2,2,2 symmetry, having two identical funnel-shaped binding sites at the dimer-dimer interface, where thyroid hormone (T4) can bind in blood plasma and CSF. TTR is typically bound to less than 1 equivalents of holo retinol binding protein. TTR is a 127-residue protein that tetramerizes under physiological conditions. TTR serves as the tertiary transporter of thyroxine in the serum and the primary carrier in the cerebrospinal fluid. TTR also transports retinol through its association with retinol binding protein. TTR forms amyloid at low pH.

As used herein, "6-carboxy-2-(3,5-dichlorophenyl)-benzoxazole" can be represented by the following chemical structure:

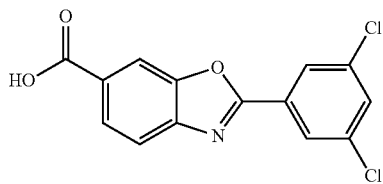 [SMILES: O=C(O)c1ccc2nc(-c3cc(Cl)cc(Cl)c3)oc2c1]

As used herein, "meglumine" can be represented by the following chemical structure:

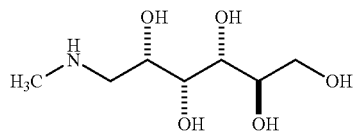

As used herein, the term "substantially pure" with reference to a particular crystalline, liquid crystalline or amorphous form means that the crystalline or amorphous form includes less than 10%, preferably less than 5%, preferably less than 3%, preferably less than 1% by weight of any other physical forms of the compound.

As used herein, the term "essentially the same" with reference to X-ray diffraction peak positions means that typical peak position and intensity variability are taken into account. For example, one skilled in the art will appreciate that the peak positions (2θ) will show some variability, typically as much as 0.1 to 0.2 degrees, as well as on the apparatus being used to measure the diffraction. Further, one skilled in the art will appreciate that relative peak intensities will show interapparatus variability as well as variability due to degree of crystallinity, preferred orientation, prepared sample surface, and other factors known to those skilled in the art, and should be taken as qualitative measures only. Similarly, as used herein, "essentially the same" with reference to solid state NMR spectra and Raman spectra is intended to also encompass the variabilities associated with these analytical techniques, which are known to those of skill in the art. For example, $^{13}C$ chemical shifts measured in solid state NMR will typically have a variability of up to 0.2 ppm for well defined peaks, and even larger for broad lines, while Raman and infrared shifts will typically have a variability of about 2 $cm^{-1}$.

The term "polymorph" refers to different crystalline forms of the same Compound and includes, but is not limited to, other solid state molecular forms including hydrates (e.g., bound water present in the crystalline structure) and solvates (e.g., bound solvents other than water) of the same compound.

The term "liquid crystal" refers to any solid substance which is ordered in two dimensions. In some instances, amorphous solids may be characterized by known techniques, including X-ray powder diffraction (XRPD) crystallography, solid state nuclear magnet resonance (ssNMR) spectroscopy, differential scanning calorimetry (DSC), or some combination of these techniques. As illustrated, below, liquid crystalline solids give diffuse XRPD patterns, typically comprised of one or two broad peaks (i.e., peaks having base widths of about 5° 2θ or greater).

The term "amorphous" refers to any solid substance which lacks order in three dimensions. In some instances, amorphous solids may be characterized by known techniques, including X-ray powder diffraction (XRPD) crystallography, solid state nuclear magnet resonance (ssNMR) spectroscopy, differential scanning calorimetry (DSC), or some combination of these techniques. As illustrated, below, amorphous solids give diffuse XRPD patterns, typically comprised of one or two broad peaks (i.e., peaks having base widths of about 5° 2θ or greater).

The term "crystalline" refers to any solid substance exhibiting three-dimensional order, which in contrast to an amorphous solid substance, gives a distinctive XRPD pattern with sharply defined peaks.

The term "solvate" describes a molecular complex comprising the drug substance and a stoichiometric or non-stoichiometric amount of one or more solvent molecules (e.g., ethanol). When the solvent is tightly bound to the drug the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex will often be non-stoichiometric.

The term "hydrate" describes a solvate comprising the drug substance and a stoichiometric or non-stoichiometric amount of water.

The term "powder X-ray diffraction pattern" or "PXRD pattern" refers to the experimentally observed diffractogram or parameters derived therefrom. Powder X-Ray diffraction patterns are characterized by peak position (abscissa) and peak intensities (ordinate).

The term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific solid form is intended to mean the 2θ values (in degrees) as measured using the X-ray diffraction experimental conditions as described herein. For example, as described herein, $CuK\alpha_1$ (wavelength 1.54056 Å) was used as the source of radiation.

The term "pharmaceutical composition" refers to a composition comprising one or more of the solid forms of Compound 1 described herein, and other chemical components, such as physiologically/pharmaceutically acceptable carriers, diluents, vehicles and/or excipients. The purpose of a pharmaceutical composition is to facilitate administration of a Compound to an organism, such as a human or other mammal.

The term "pharmaceutically acceptable" "carrier", "diluent", "vehicle", or "excipient" refers to a material (or materials) that may be included with a particular pharmaceutical agent to form a pharmaceutical composition, and may be solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methyl methacrylate and the like.

Solid Forms of Compound 1

The solid forms of Compound 1 can be characterized by one or more of the following: powder X-ray diffraction pattern (i.e., X-ray diffraction peaks at various diffraction angles (2θ)), solid state nuclear magnetic resonance (NMR) spectral pattern, Raman spectral diagram pattern, Infrared spectral pattern, aqueous solubility, light stability under International Conference on Harmonization (ICH) high intensity light conditions, and physical and chemical storage stability. For example, a crystalline form, a two-dimensionally ordered liquid crystalline form and an amorphous form (discussed below) of Compound 1 were each characterized by the positions and relative intensities of peaks in their powder X-ray diffraction patterns.

The powder X-ray diffraction patterns of the solid forms of Compound 1 was collected using a Bruker D8 diffractometer equipped with a Cu radiation source, fixed slits (divergence=1.0 mm, anti-scatter=0.6 mm, and receiving=0.6 mm) and a scintillation counter detector. Data were collected in the Theta-Theta goniometer at the Cu wavelength $K\alpha_1$=1.54056 Å from 3.0 to 40.0 degrees 2-Theta using a step size of 0.040 degrees and a step time of 2.0 second. X-ray tube voltage and amperage were set at 40 kV and 40 mA respectively. Samples were prepared by placement in a Nickel Disk (Gasser & Sons, Inc. Commack, N.Y.) and rotated during data collection. Data were collected and analyzed using Bruker DIFFRAC Plus software (Version 2.6). PXRD data files (.raw) were not processed prior to peak searching. Generally, a Threshold value of 1 and a Width value of 0.3 were used to make preliminary peak assignments. The output of automated assignments was visually checked to ensure validity and adjustments manually made if necessary. Additionally, peaks were manually assigned within spectra if appropriate.

To perform an X-ray diffraction measurement on a Bragg-Brentano instrument like the Bruker system used for measurements reported herein, the sample is typically placed into a holder which has a cavity. The sample powder is pressed by a glass slide or equivalent to ensure a random surface and proper sample height. The sample holder is then placed into the instrument. The incident X-ray beam is directed at the sample, initially at a small angle relative to the plane of the holder, and then moved through an arc that continuously increases the angle between the incident beam and the plane of the holder. Measurement differences associated with such X-ray powder analyses result from a variety of factors including: (a) errors in sample preparation (e.g., sample height); (b) instrument errors (e.g., flat sample errors); (c) calibration errors; (d) operator errors (including those errors present when determining the peak locations); and (e) the nature of the material (e.g., preferred orientation and transparency errors). Calibration errors and sample height errors often result in a shift of all the peaks in the same direction. Small differences in sample height when using a flat holder will lead to large displacements in PXRD peak positions. A systematic study showed that, using a Shimadzu XRD-6000 in the typical Bragg-Brentano configuration, sample height difference of 1 mm led to peak shifts as high as 1 degree (2θ (Chen et al., J Pharmaceutical and Biomedical Analysis 26:63 (2001)). These shifts can be identified from the X-ray diffractogram and can be eliminated by compensating for the shift (applying a systematic correction factor to all peak position values) or recalibrating the instrument. As mentioned above, it is possible to rectify measurements from the various machines by applying a systematic correction factor to bring the peak positions into agreement. In general, this correction factor will bring the measured peak positions from the Bruker into agreement with the expected peak positions and may be in the range of 0 to 0.2 degrees (2θ).

One of skill in the art will appreciate that the peak positions (2θ) will show some inter-apparatus variability, typically as much as 0.1 to 0.2 degrees (2θ). Accordingly, where peak positions (2θ) are reported, one of skill in the art will recognize that such numbers are intended to encompass such inter-apparatus variability. Furthermore, where the crystalline forms of the present invention are described as having a powder X-ray diffraction peak position essentially the same as that shown in a given figure, the term "essentially the same" is also intended to encompass such inter-apparatus variability in diffraction peak positions. Further, one skilled in the art will appreciate that relative peak intensities will show inter-apparatus variability as well as variability due to the degree of crystallinity, preferred orientation, prepared sample surface, and other factors known to those skilled in the art, and should be taken as qualitative measures only.

The solid forms of the present invention can also be characterized Raman spectroscopy. Raman spectra were collected using a Nicolet NXR FT-Raman accessory attached to an FT-IR bench. The spectrometer is equipped with a 1064 nm Nd:YVO4 laser and a liquid nitrogen cooled Germanium detector. Prior to data acquisition, instrument performance and calibration verifications were conducted using polystyrene. Samples were analyzed in glass NMR tubes that were spun during spectral collection. The spectra were collected using 0.5 W of laser power and 400 co-added scans. The collection range was 3700-50 cm-1. Spectra were recorded using 2 cm-1 resolution, and Happ-Genzel apodization. Peaks were manually identified using the Thermo Nicolet Omnic 7.4 software. Peak positions were picked at the peak maxima. Relative intensity values were classified as strong (S), medium (M) and weak (W) using the following criteria: strong (1.00-0.50); medium (0.49-0.10) and weak (0.09 and below).

The solid forms of the present invention can also be characterized using Infrared (IR) spectroscopy. The IR spectra were acquired using a Nicolet 6700 FTIR spectrometer equipped with a KBr beamsplitter and a d-TGS KBr detector. A Specac Golden Gate Mk II single reflection diamond ATR accessory was used for sampling. A nitrogen purge was connected to the IR bench as well as the ATR accessory. The Golden Gate ATR anvil was in the up position when the air background is collected. Powder samples were compressed against the diamond window by the Golden Gate anvil. Approximately 50 cN·m of torque was applied to the sample when the anvil was completely compressed into the sample. Spectra were collected at 2 $cm^{-1}$ resolution with 256 co-added scans. The collection range was 4000-525 $cm^{-1}$. Happ-Genzel apodization was used. No additional sample preparation is needed with the ATR technique. Peaks were manually identified using the Thermo Nicolet Omnic 7.4 software. Peak positions were picked at the peak maxima. Intensity values were classified as strong (S), medium (M) and weak (W) using the following criteria: strong (1.00-0.50); medium (0.49-0.40) and weak (0.39 and below). Features in the region between 2400-1900 $cm^{-1}$ are present in all spectra run by the Golden Gate d-ATR, so peaks in this region were not used for solid form identification and are not included in the peak list (Ferrer, N.; Nogués-Carulla, J. M. *Diamond and Related Materials* 1996, 5, 598-602. Thongnopkun, P.; Ekgasit, S.

*Diamond and Related Materials* 2005, 14, 1592-1599. Pike Technologies Technical Note: *Pike Reflections*, Winter 2002, Vol. 7/1; www.piketech.com).

The different forms of the present invention can also be characterized using solid state NMR spectroscopy.

The $^{13}C$ solid state spectra for the crystalline and amorphous forms can be collected as follows. Approximately 80 mg of sample were tightly packed into a 4 mm $ZrO_2$ rotor. Spectra were collected on a Bruker-Biospin 4 mm CPMAS probe positioned into a wide-bore Bruker-Biospin Avance III 500 MHz ($^1H$ frequency) NMR spectrometer. The packed rotor was oriented at the magic angle and spun at 15.0 kHz. The sample was cooled to 25.0° C. with a direct stream of nitrogen. The $^{13}C$ solid state spectra were collected using a proton decoupled cross-polarization magic angle spinning (CPMAS) experiment. The cross-polarization contact time was set to 2.0 ms. A proton decoupling field of approximately 100 kHz was applied during acquisition. 2048 scans were collected with a 6.5 second recycle delay. The spectra were referenced using an external standard of crystalline adamantane, setting its upfield resonance to 29.5 ppm. Automatic peak picking was performed using Bruker-BioSpin TopSpin version 3.0 software. Generally, a threshold value of 10 was used to preliminary select peaks. The output of the automated peak picking was visually checked to ensure validity and adjustments manually made if necessary.

The $^{13}C$ solid state spectra for the liquid crystalline form can be collected as follows. Approximately 10 mg of sample was centered in a 4 mm $ZrO_2$ rotor. Spectra were collected on a Bruker-Biospin 4 mm CPMAS probe positioned into a wide-bore Bruker-Biospin Avance III 500 MHz ($^1H$ frequency) NMR spectrometer. The packed rotor was oriented at the magic angle and spun at 6.0 kHz. The sample was cooled to 25.0° C. with a direct stream of nitrogen. The $^{13}C$ solid state spectra were collected using a proton decoupled cross-polarization magic angle spinning (CPMAS) experiment using total suppression of spinning side-bands (TOSS). The cross-polarization contact time was set to 2.0 ms. A proton decoupling field of approximately 85 kHz was applied during acquisition. 10240 scans were collected with a 3 second recycle delay. The spectrum was referenced using an external standard of crystalline adamantane, setting its upfield resonance to 29.5 ppm. Automatic peak picking was performed using Bruker-BioSpin TopSpin version 3.0 software. Generally, a threshold value of 10 was used to preliminary select peaks. The output of the automated peak picking was visually checked to ensure validity and adjustments manually made if necessary.

One of skill in the art will also recognize that crystalline forms of a given compound can exist in substantially pure forms of a single polymorph, but can also exist in a crystalline form that comprises two or more different polymorphs or amorphous forms. Where a solid form comprises two or more polymorphs, the X-ray diffraction pattern will have peaks characteristic of each of the individual polymorphs of the present invention. For example, a solid form that comprises two polymorphs will have a powder X-ray diffraction pattern that is a convolution of the two X-ray diffraction patterns that correspond to the substantially pure solid forms. For example, a solid form of Compound 1 can contain a first and second solid form where the solid form contains at least 10% by weight of the first polymorph. In a further example, the solid form contains at least 20% by weight of the first polymorph. Even further examples contain at least 30%, at least 40%, or at least 50% by weight of the first polymorph. One of skill in the art will recognize that many such combinations of several individual polymorphs and amorphous forms in varying amounts are possible.

Crystalline Form

A crystalline form of Compound 1 is a fully crystalline, non-hygroscopic, anhydrous, mono-meglumine salt form that can be produced as described in Example 1. Importantly, this form has advantages over the free acid and other solid forms of Compound 1. For example, the crystalline form has improved solubility (>3.4 mg/mL in unbuffered water) compared to the free acid (<11 ug/mL in unbuffered water. In addition, in comparison to the other solid forms described herein, the crystalline form has improved handling properties, as it is non-hygroscopic.

The crystalline form of Compound 1 was characterized by the PXRD pattern shown in FIG. 1A, which was measured on Bruker D8 diffractometer equipped with a Cu radiation source, fixed slits (divergence=1.0 mm, anti-scatter=0.6 mm, and receiving=0.6 mm) and a scintillation counter detector. The PXRD pattern of the crystalline form, expressed in terms of the degree (2θ) and relative intensities with a relative intensity of 10.0%, is shown in FIG. 1B. The relative intensities may change depending on the crystal size and morphology.

Figure 4A:
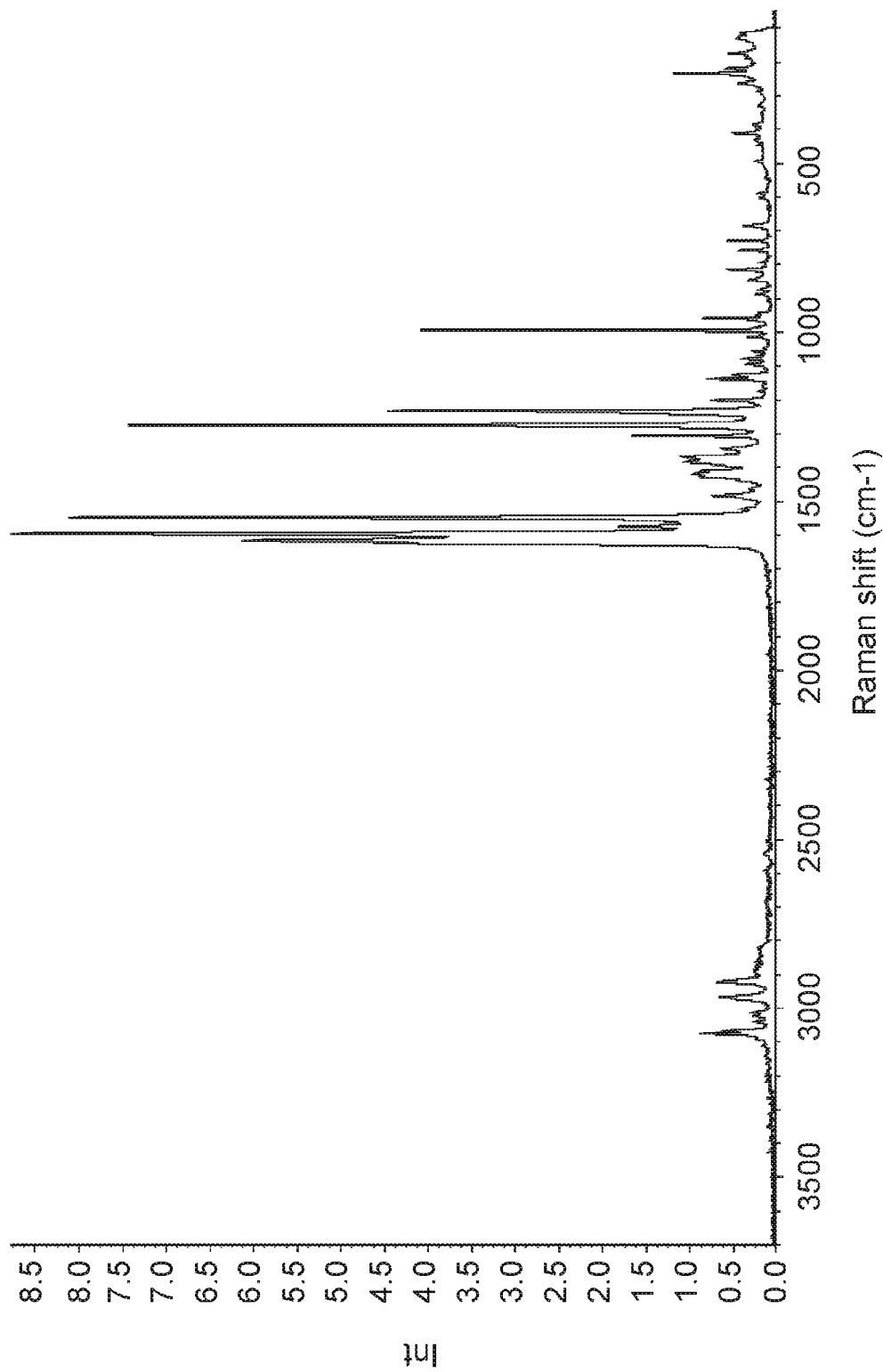
FIG. 4 depicts (a) a Raman spectrum of crystalline Compound 1 carried out on a Nicolet NXR FT-Raman spectrometer equipped with a 1064 nm Nd:YVO$_4$ laser and a liquid cooled Germanium detector and (b) a corresponding peak list.

The crystalline form of Compound 1 was also characterized by the Raman spectral pattern shown in FIG. 4A, which was carried out on a Nicolet NXR FT-Raman spectrometer equipped with a 1064 nm Nd:$YVO_4$ laser and a liquid cooled Germanium detector. The Raman spectral peaks of the crystalline form of Compound 1 are shown in FIG. 4B.

Figure 7A:
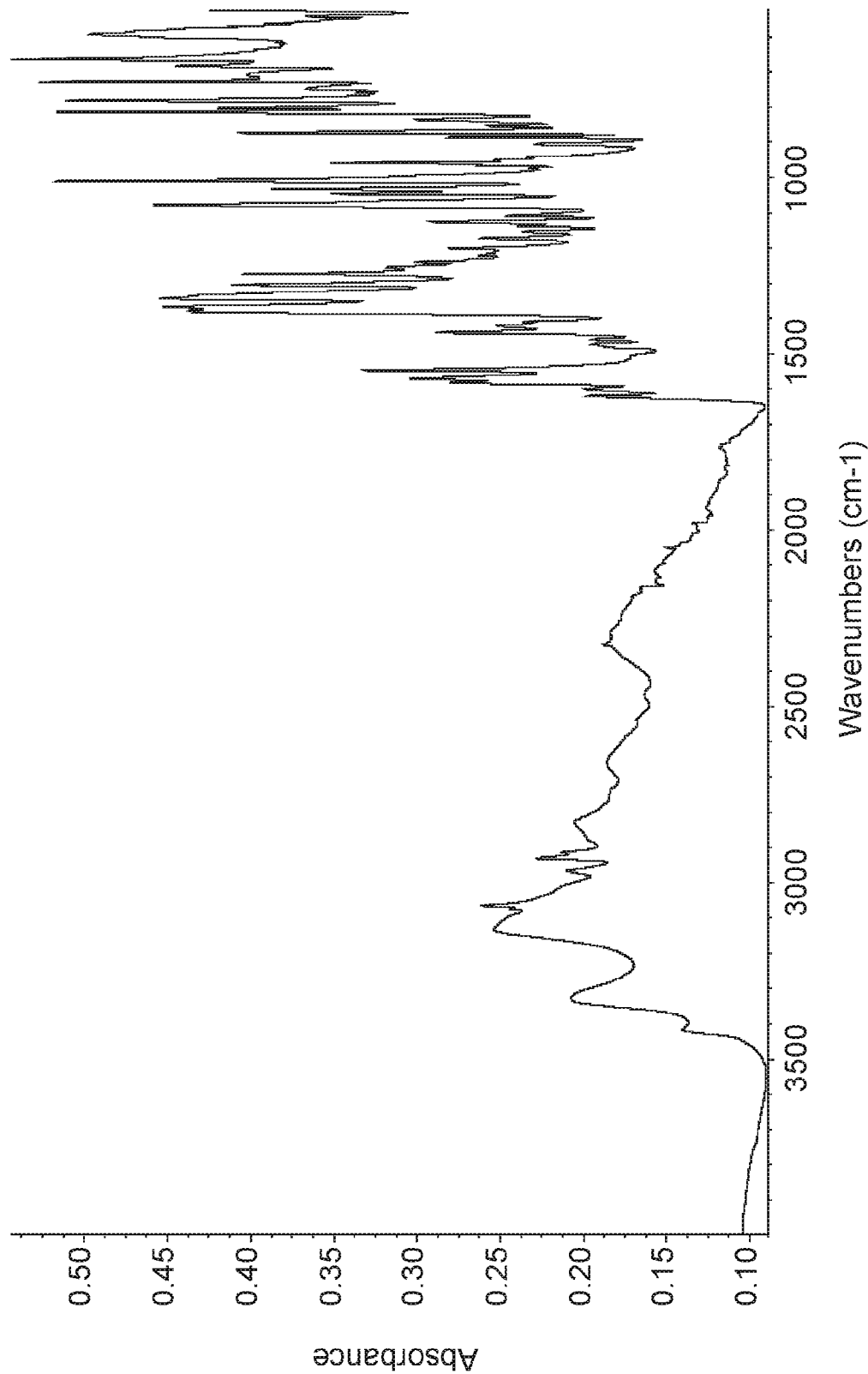
FIG. 7 depicts (a) a infrared spectrum of crystalline Compound 1 carried out on a Nicolet 6700 FTIR spectrometer equipped with a KBr beamsplitter and a d-TGS KBR detector and (b) a corresponding peak list.

The crystalline form of Compound 1 was also characterized by the infrared spectral pattern shown in FIG. 7A, which was carried out on a Nicolet 6700 FTIR spectrometer equipped with a KBr beamsplitter and a d-TGS KBR detector. The infrared spectral peaks of the crystalline form of Compound 1 are shown in FIG. 7B.

Figures 10A, 10B:
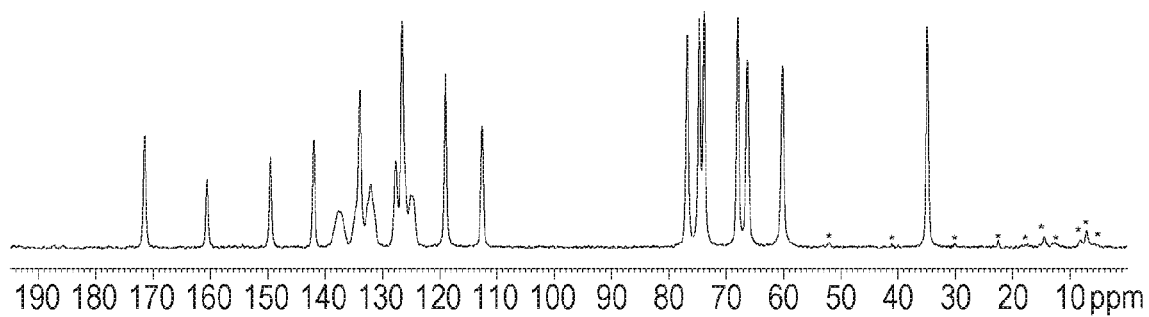
FIG. 10 depicts (a) a $^{13}$C solid state NMR spectrum of crystalline Compound 1 carried out on a Bruker-Biospin 4 mm CPMAS probe positioned into a wide-bore Bruker-Biospin Avance III 500 MHz NMR spectrometer and (b) a corresponding peak list. The chemical shifts are referenced to an external sample of solid phase adamantane at 29.5 ppm.

The crystalline form of Compound 1 was also characterized by the solid state NMR spectral pattern shown in FIG. 10A, which was carried out on a Bruker-Biospin 4 mm CPMAS probe positioned into a wide-bore Bruker-Biospin Avance III 500 MHz NMR spectrometer. The $^{13}C$ chemical shifts of the crystalline form of Compound 1 are shown in FIG. 10B.

Liquid Crystalline Form

A liquid crystalline form of Compound 1 can be produced as described in Example 2.

Figure 2A:
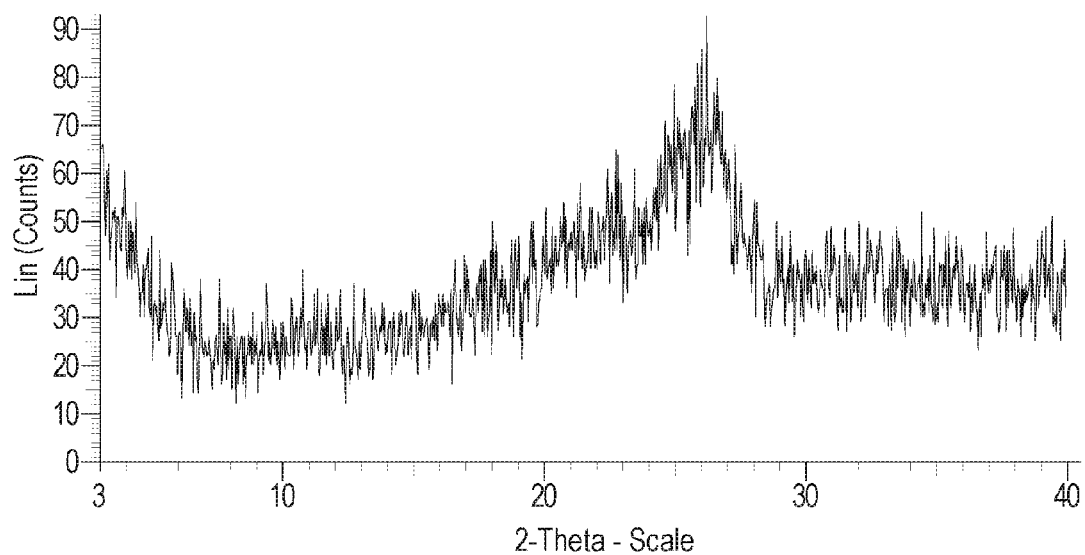
FIG. 2 depicts (a) a XRPD pattern of liquid crystalline Compound 1 carried out on a Bruker D8 diffractometer and (b) shows the processed version of the same.
Figure 2B:
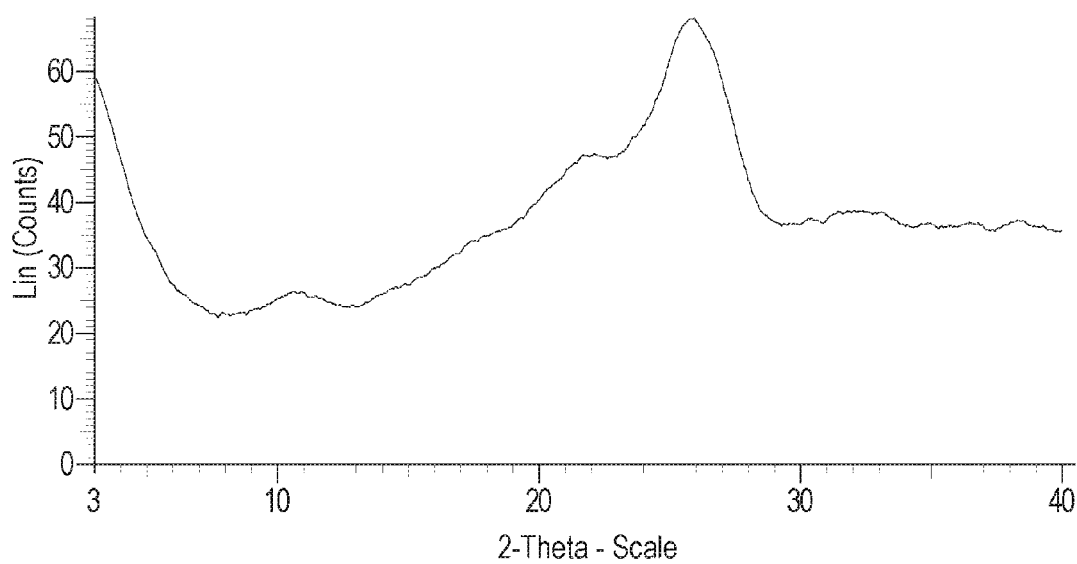

The liquid crystalline form of Compound 1 was characterized by the PXRD pattern shown in FIGS. 2A and 2B, which was measured on Bruker D8 diffractometer equipped with a Cu radiation source, fixed slits (divergence=1.0 mm, anti-scatter=0.6 mm, and receiving=0.6 mm) and a scintillation counter detector.

The liquid crystalline form of Compound 1 was also characterized by the Raman spectral pattern shown in FIG. 5A, which was carried out on a Nicolet NXR FT-Raman spectrometer equipped with a 1064 nm Nd:$YVO_4$ laser and a liquid cooled Germanium detector. The Raman spectral peaks of the liquid crystalline form of Compound 1 are shown in FIG. 5B.

Figure 8A:
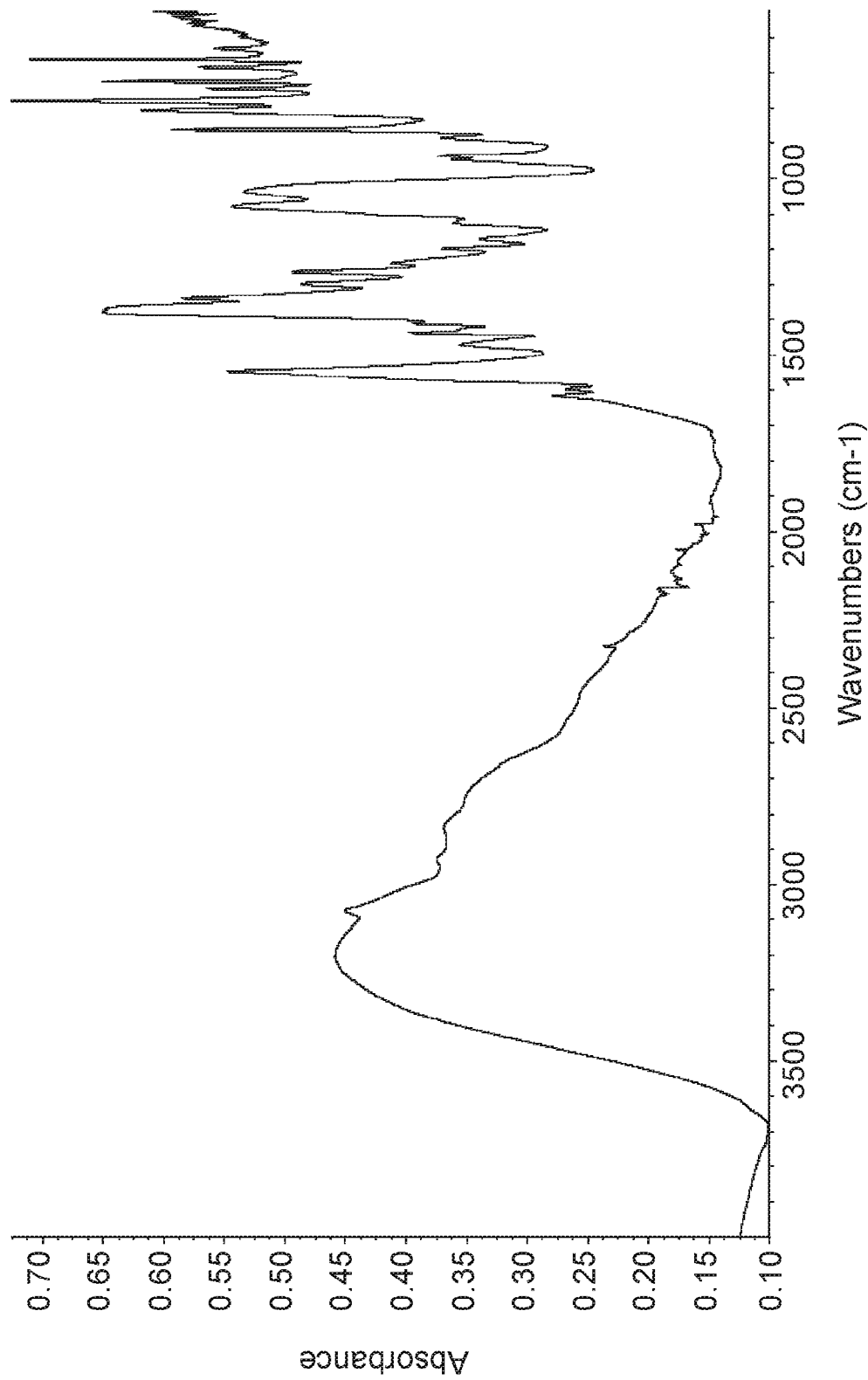
FIG. 8 depicts (a) a infrared spectrum of liquid crystalline Compound 1 carried out on a Nicolet 6700 FTIR spectrometer equipped with a KBr beamsplitter and a d-TGS KBR detector and (b) a corresponding peak list.

The liquid crystalline form of Compound 1 was also characterized by the infrared spectral pattern shown in FIG. 8A, which was carried out on a Nicolet 6700 FTIR spectrometer equipped with a KBr beamsplitter and a d-TGS KBR detector. The infrared spectral peaks of the liquid crystalline form of Compound 1 are shown in FIG. 8B.

Figures 11A, 11B:
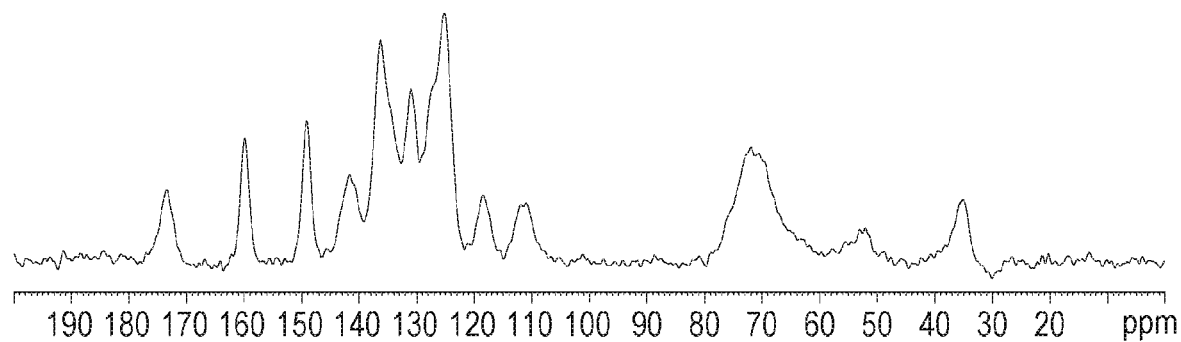
FIG. 11 depicts (a) a $^{13}$C solid state NMR spectrum of liquid crystalline Compound 1 carried out on a Bruker-Biospin 4 mm CPMAS probe positioned into a wide-bore Bruker-Biospin Avance III 500 MHz NMR spectrometer and (b) a corresponding peak list. The chemical shifts are referenced to an external sample of solid phase adamantane at 29.5 ppm.

The liquid crystalline form of Compound 1 was also characterized by the solid state NMR spectral pattern shown in FIG. 11A, which was carried out on a Bruker-Biospin 4 mm CPMAS probe positioned into a wide-bore Bruker-Biospin Avance III 500 MHz NMR spectrometer. The $^{13}$C chemical shifts of the liquid crystalline form of Compound 1 are shown in FIG. 11B.

Amorphous Form

An amorphous form of Compound 1 can be produced as described in Example 3.

Figure 3A:
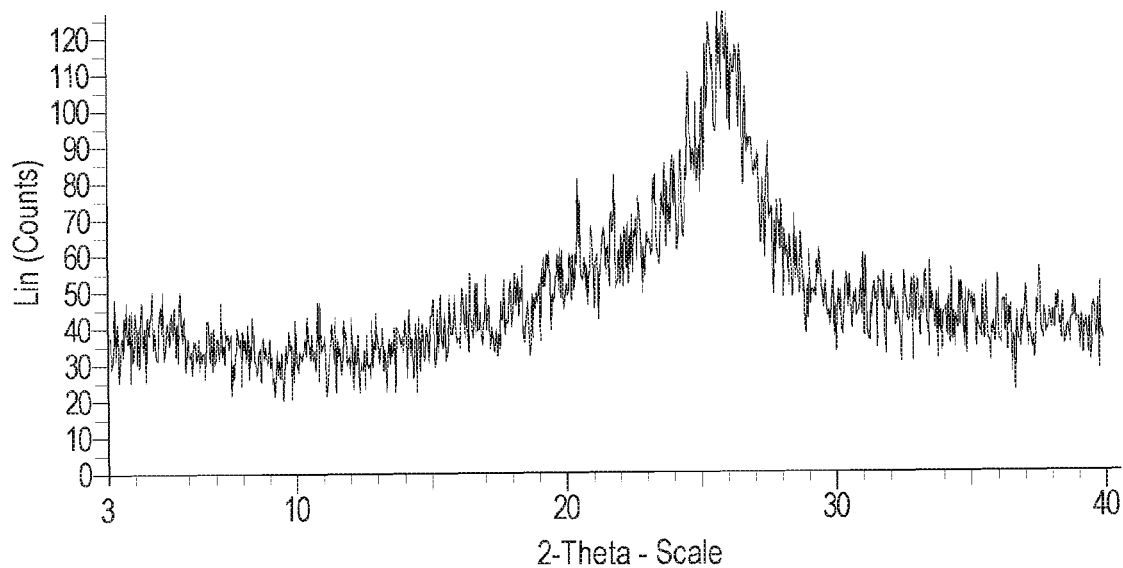
FIG. 3 depicts (a) a XRPD pattern of amorphous Compound 1 carried out on a Bruker D8 diffractometer and (b) shows the processed version of the same.
Figure 3B:
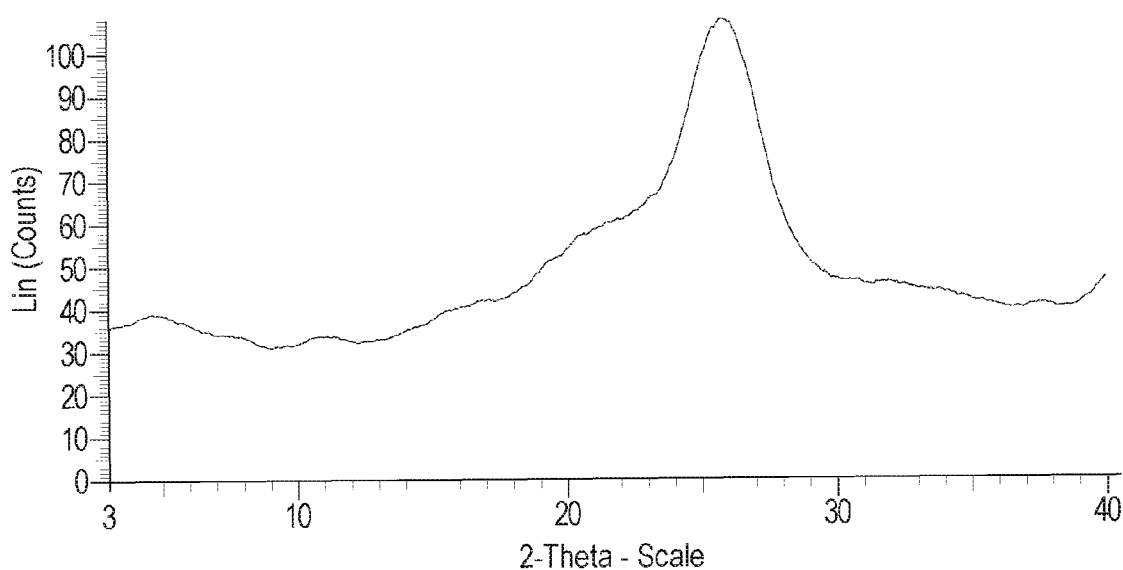

The amorphous form of Compound 1 was characterized by the PXRD pattern shown in FIGS. 3A and 3B, which was measured on Bruker D8 diffractometer equipped with a Cu radiation source, fixed slits (divergence=1.0 mm, anti-scatter=0.6 mm, and receiving=0.6 mm) and a scintillation counter detector.

The amorphous form of Compound 1 was also characterized by the Raman spectral pattern shown in FIG. 6A, which was carried out on a Nicolet NXR FT-Raman spectrometer equipped with a 1064 nm Nd:YVO$_4$ laser and a liquid cooled Germanium detector. The Raman spectral peaks of the amorphous form of Compound 1 are shown in FIG. 6B.

Figure 9A:
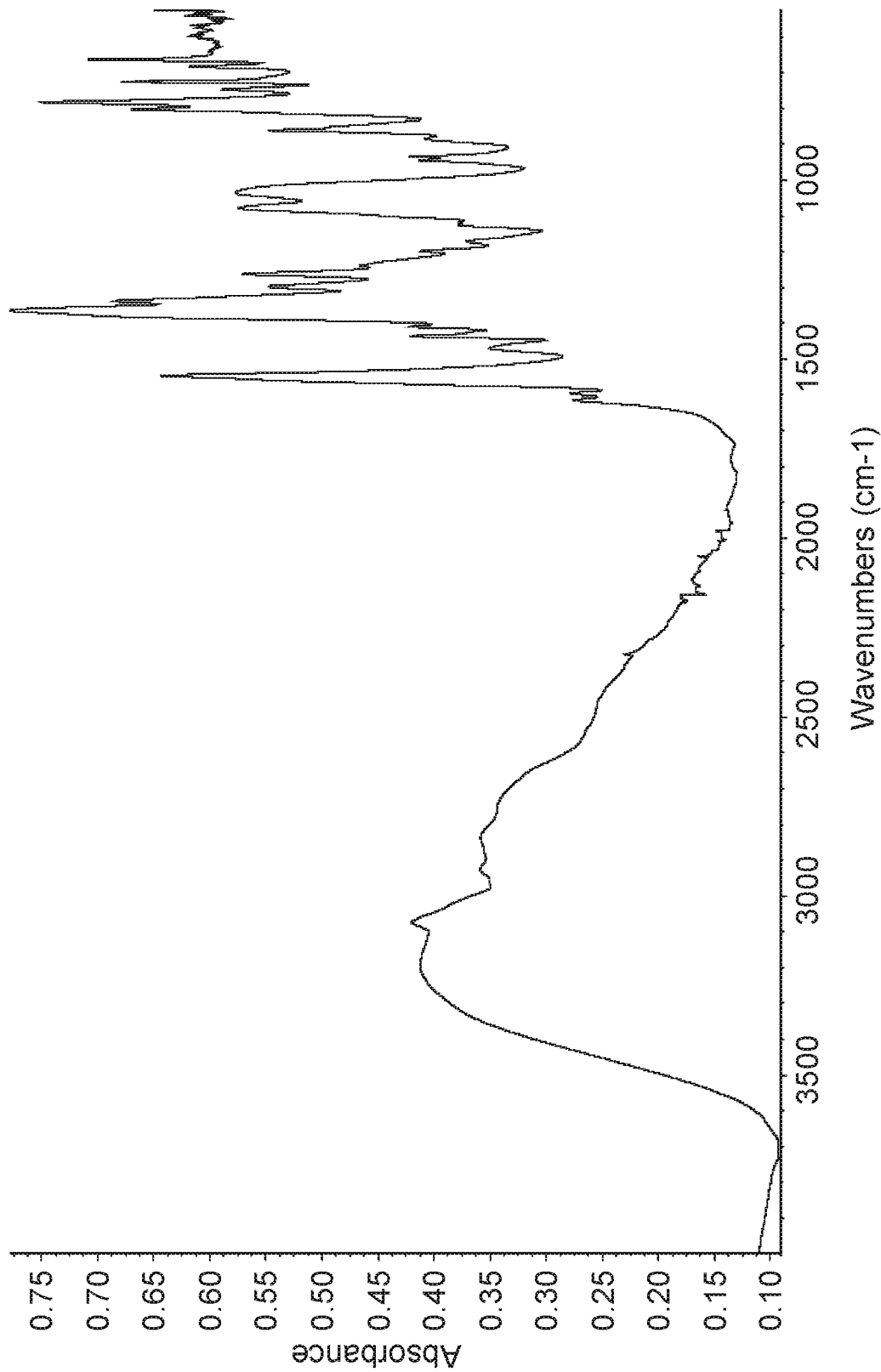
FIG. 9 depicts (a) a infrared spectrum of amorphous Compound 1 carried out on a Nicolet 6700 FTIR spectrometer equipped with a KBr beamsplitter and a d-TGS KBR detector and (b) a corresponding peak list.

The amorphous form of Compound 1 was also characterized by the infrared spectral pattern shown in FIG. 9A, which was carried out on a Nicolet 6700 FTIR spectrometer equipped with a KBr beamsplitter and a d-TGS KBR detector. The infrared spectral peaks of the amorphous form of Compound 1 are shown in FIG. 9B.

Figures 12A, 12B:
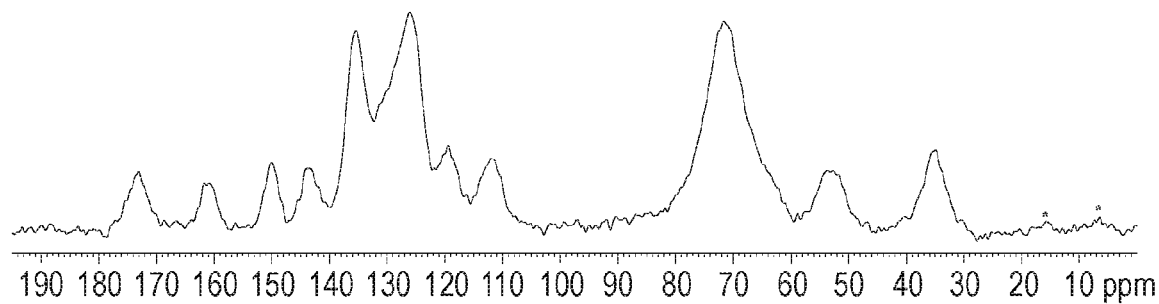
FIG. 12 depicts (a) a $^{13}$C solid state NMR spectrum of amorphous Compound 1 carried out on a Bruker-Biospin 4 mm CPMAS probe positioned into a wide-bore Bruker-Biospin Avance III 500 MHz NMR spectrometer and (b) a corresponding peak list. The chemical shifts are referenced to an external sample of solid phase adamantane at 29.5 ppm.

The amorphous form of Compound 1 was also characterized by the solid state NMR spectral pattern shown in FIG. 12A, which was carried out on a Bruker-Biospin 4 mm CPMAS probe positioned into a wide-bore Bruker-Biospin Avance III 500 MHz NMR spectrometer. The $^{13}$C chemical shifts of the amorphous form of Compound 1 are shown in FIG. 12B.

Pharmaceutical Compositions

The active agents (i.e., the solid forms of Compound 1 described herein) of the invention may be formulated into pharmaceutical compositions suitable for mammalian medical use. Any suitable route of administration may be employed for providing a patient with an effective dosage of any of the solid forms of Compound 1. For example, peroral or parenteral formulations and the like may be employed. Dosage forms include capsules, tablets, dispersions, suspensions and the like, e.g. enteric-coated capsules and/or tablets, capsules and/or tablets containing enteric-coated pellets of Compound 1. In all dosage forms, solid forms of Compound 1 can be admixed with other suitable constituents. The compositions may be conveniently presented in unit dosage forms, and prepared by any methods known in the pharmaceutical arts. Pharmaceutical compositions of the invention comprise a therapeutically effective amount of the active agent and one or more inert, pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20™" and "TWEEN 80™", and Pluronic® F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations).

Other pharmaceutical excipients and/or additives suitable for use in the compositions according to the invention are listed in Remington: The Science & Practice of Pharmacy, 19th ed., Williams & Williams, (1995), and in the "Physician's Desk Reference", 52nd ed., Medical Economics, Montvale, N.J. (1998), and in "Handbook of Pharmaceutical Excipients", 3rd. Ed., Ed. A. H. Kibbe, Pharmaceutical Press, 2000. The active agents of the invention may be formulated in compositions including those suitable for oral, rectal, topical, nasal, ophthalmic, or parenteral (including intraperitoneal, intravenous, subcutaneous, or intramuscular injection) administration.

The amount of the active agent in the formulation will vary depending upon a variety of factors, including dosage form, the condition to be treated, target patient population, and other considerations, and will generally be readily determined by one skilled in the art. A therapeutically effective amount will be an amount necessary to inhibit transthyretin (TTR) dissociation (i.e. prevents dissociation of the native TTR tetramer into monomers). Compositions will generally contain anywhere from about 0.001% by weight to about 99% by weight active agent, preferably from about 0.01% to about 5% by weight active agent, and more preferably from about 0.01% to 2% by weight active agent, and will also depend upon the relative amounts of excipients/additives contained in the composition.

A pharmaceutical composition of the invention is administered in conventional dosage form prepared by combining a therapeutically effective amount of an active agent as an active ingredient with one or more appropriate pharmaceutical carrier according to conventional procedures. These procedures may involve mixing granulating and compressing or dissolving the ingredients as appropriate to the desired preparation.

The pharmaceutical carrier(s) employed may be either solid or liquid. Exemplary solid carriers include lactose, sucrose, talc, gelatin, agar, pectin, acacia, magnesium stearate, stearic acid and the like. Exemplary liquid carriers include syrup, peanut oil olive oil, water and the like. Similarly, the carrier(s) may include time-delay or time release materials known in the art, such as glyceryl monostearate or glyceryl distearate alone or with a wax, ethylcellulose, hydroxypropylmethylcellulose, methylmethacrylatt and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an active agent can be dissolved in an aqueous solution of an organic or inorganic base, such as a 0.3 M solution of meglumine. If a soluble salt form is not available, the active agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from 0-60% of the total volume. The composition may also be in the form of a solution of a salt form of the active agent in an appropriate aqueous vehicle such as water or isotonic saline or dextrose solution.

It will be appreciated that the actual dosages of Compound 1 used in the compositions of this invention will vary according to the particular solid form being used, the particular composition formulated, the mode of administration and the particular site, host and disease being treated. Those skilled in the art using conventional dosage-determination tests in view of the experimental data for an agent can ascertain optimal dosages for a given set of conditions. For oral administration, an exemplary daily dose generally employed is from about 0.001 to about 1000 mg/kg of body weight, more preferably from about 0.001 to about 50 mg/kg body weight, with courses of treatment repeated at appropriate intervals. Administration of prodrugs is typically dosed at weight levels that are chemically equivalent to the weight levels of the fully active form. In the practice of the invention, the most suitable route of administration as well as the magnitude of a therapeutic dose will depend on the nature and severity of the disease to be treated. The dose, and dose frequency, may also vary according to the age, body weight, and response of the individual patient. In general, a suitable oral dosage form may cover a dose range from 0.5 mg to 100 mg of active ingredient total daily dose, administered in one single dose or equally divided doses. A preferred amount of Compound 1 in such formulations is from about 0.5 mg to about 20 mg, such as from about 1 mg to about 10 mg or from about 1 mg to about 5 mg.

The compositions of the invention may be manufactured in manners generally known for preparing pharmaceutical compositions, e.g., using conventional techniques such as mixing, dissolving, granulating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations that can be used pharmaceutically.

For oral administration, a solid form of Compound 1 can be formulated by combining the active agent with pharmaceutically acceptable carriers known in the art. Such carriers enable the compounds of the invention to be formulated as tablets, pills, capsules, gels, syrups, slurries, suspensions and the like, for oral ingestion by a patient to be treated. Pharmaceutical preparations for oral use can be obtained using a solid excipient in admixture with the active agent, optionally grinding the resulting mixture, and processing the mixture of granules after adding suitable auxiliaries. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration to the eye, the active agent is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be, for example, an ointment, vegetable oil, or an encapsulating material. An active agent of the invention may also be injected directly into the vitreous and aqueous humor or subtenon.

Alternatively, the active ingredient may be in powder form for constitution with a suitable vehicle, e.g., sterile pyrogen-free water, before use. The compounds may also be formulated in rectal or vaginal compositions such as suppositories or retention enemas, e.g., containing conventional suppository bases such as cocoa butter or other glycerides.

In addition to the formulations described above, the solid forms may also be formulated as a depot preparation. Such long-acting formulations may be administered by implantation (for example, subcutaneously or intramuscularly) or by intramuscular injection. Thus, for example, the solid forms may be formulated with suitable polymeric or hydrophobic materials (for example, as an emulsion in an acceptable oil) or ion-exchange resins, or as sparingly soluble derivatives, for example, as a sparingly soluble salt.

Additionally, solid forms of Compound 1 may be delivered using a sustained-release system, such as semi-permeable matrices of solid hydrophobic polymers containing the therapeutic agent. Various sustained-release materials have been established and are known by those skilled in the art.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Applicants have discovered that 6-carboxy-2-(3,5-dichlorophenyl)-benzoxazole alone can form a gel on contact with aqueous vehicles, such as water, phosphate buffer and hydrochloric acid. Without wishing to be bound by theory, it appears that such gel formation, upon oral administration, can hinder dissolution and/or bioavailability of such compounds, leading to, for example, stomach compaction and non-proportional plasma levels of drug in the subject as compared to the dose administered. Applicants have discovered pharmaceutical compositions of solid forms of Compound 1 (6-carboxy-2-(3,5-dichlorophenyl)-benzoxazole meglumine) that surprisingly can be comparatively resistant to gel formation and stomach compaction, and can have comparatively greater dissolution and bioavailability, and can deliver drug levels proportional to the administered dose. Moreover, in certain embodiments, the pharmaceutical compositions of Compound 1 can be stable to accelerated aging conditions, such as elevated temperature and humidity. Consequently, the pharmaceutical compositions herein are also contemplated for use in or further combination with any conventional formulation or route or method of administration where contact with water or other aqueous vehicles may occur, e.g., contact with blood or other body fluids as in various forms of parenteral administration (e.g., contact with blood in intravenous administration, implants, and the like), contact with mucous membranes (e.g., suppositories via vaginal or rectal administration, dry powder aerosols for pulmonary administration, transdermal patches or lozenges applied to mucous membranes, and the like). In such routes of administration, the benefits of the certain pharmaceutical compositions, such as resistance to gel formation, greater dissolution and bioavailability, dose proportionality, stability to storage, or the like may be beneficial.

For example, in certain embodiments, the pharmaceutical composition comprise a solid form of Compound 1 and a polyethylene glycol having an average molecular weight of between about 100 and about 1000, characterized in that the solid form in the pharmaceutical composition has, compared to the solid form alone, a greater dispersibility in water or greater resistance to gel formation on contact with water. In certain embodiments, the molecular weight of the polyethylene glycol is about 400.

In certain embodiments, the invention relates to any of the aforementioned pharmaceutical compositions, wherein said composition comprises PEG 400, Span™ 80 and/or polysorbate 80.

In certain embodiments, the invention relates to any of the aforementioned pharmaceutical compositions, wherein said solid form of Compound 1 is the crystalline form. In certain embodiments, the invention relates to any of the aforementioned pharmaceutical compositions, wherein said solid form of Compound 1 is the liquid crystalline form. In certain embodiments, the invention relates to any of the aforementioned pharmaceutical compositions, wherein said solid form of Compound 1 is the amorphous form.

Articles of Manufacture

The solid forms of Compound 1 may be packaged as articles of manufacture containing packaging material, a solid form of Compound 1 as provided herein, which is effective for modulating TTR folding, or for treatment, prevention or amelioration of one or more symptoms of TTR mediated diseases or disorders, or diseases or disorders in which TTR misfolding, is implicated, within the packaging material, and a label that indicates that the solid form of Compound 1 is used for modulating TTR folding, or for treatment, prevention or amelioration of one or more symptoms of TTR mediated diseases or disorders, or diseases or disorders in which TTR misfolding is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A variety of treatments for any disease or disorder in which TTR misfolding is implicated as a mediator or contributor to the symptoms or cause.

In certain embodiments, the invention relates to any of the aforementioned articles of manufacture, wherein said solid form of Compound 1 is the crystalline form. In certain embodiments, the invention relates to any of the aforementioned articles of manufacture, wherein said solid form of Compound 1 is the liquid crystalline form. In certain embodiments, the invention relates to any of the aforementioned articles of manufacture, wherein said solid form of Compound 1 is the amorphous form.

In Vitro Biological Testing

A number of in vitro tests can be used to evaluate the solid forms for their ability to stabilize transthyretin tetramers or prevent formation of fibrils. The tests can include a fibril formation assay, a plasma selectivity assay, determination of the three-dimensional structure of a transthyretin compound complex (e. g. by X-ray crystallography), kinetics of transthyretin tetramer dissociation or fibril formations, and determining the stoichiometry and energetics of transthyretin compound interactions, by, for example, centrifugation or calorimetry. Details of exemplary in vitro assays are provided in U.S. Pat. Nos. 7,214,695 and 7,214,696; and in U.S. Patent Application Publication No. 2010/0120919 (all of which are hereby incorporated by reference in their entireties).

Methods of Using the Solid Forms of the Invention

Solid forms of Compound 1 are useful for stabilizing the protein transthyretin (TTR), dissociation of which is implicated in TTR amyloidosis (i.e., prevents dissociation of the native TTR tetramer into monomers, which results in the inhibition of TTR amyloid fibril formation), thus providing treatments for transthyretin amyloid diseases in mammals, including humans.

At least some amyloid diseases appear to be caused by the deposition of any one of more than 20 nonhomologous proteins or protein fragments, ultimately affording a fibrillar cross-β-sheet quaternary structure. Formation of amyloid fibrils from a normally folded protein like transthyretin requires protein misfolding to produce an assembly-competent intermediate. The process of transthyretin (TTR) amyloidogenesis appears to cause senile systemic amyloidosis (SSA), familial amyloid polyneuropathy (FAP) and familial amyloid cardiomyopathy (FAC). SSA is associated with the deposition of wild-type TTR, while FAP and FAC are caused by the amyloidogenesis of one of over 80 TTR variants. See, for example, Colon, W.; Kelly, J. W. *Biochemistry* 1992, 31, 8654-60; Kelly, J. W. *Curr. Opin. Struct. Biol.* 1996, 6, 11-7; Liu, K.; et al. *Nat. Struct. Biol.* 2000, 7, 754-7; Westermark, P.; et al. *Proc. Natl. Acad. Sci. U.S.A.* 1990, 87, 2843-5; Saraiva, M. J.; et al. *J. Clin. Invest.* 1985, 76, 2171-7; Jacobson, D. R.; et al. *N. Engl. J. Med.* 1997, 336, 466-73; Buxbaum, J. N.; Tagoe, C. E. *Ann. Rev. Med.* 2000, 51, 543-569; and Saraiva, M. J. *Hum. Mutat.* 1995, 5, 191-6, each of which is incorporated by reference in its entirety. Additional TTR amyloid diseases include cardiac amyloidosis following liver transplantation, peripheral nerve amyloidosis following liver transplantation, leptomeningeal amyloidosis, transthyretin mutant-associated carpal tunnel syndrome, vitreous deposition, and transthyretin mutant-associated skin amyloidosis.

Therapeutically effective amounts of Compound 1 may be administered, typically in the form of a pharmaceutical composition, to treat diseases mediated by modulation or regulation of TTR dissociation. An "effective amount" is intended to mean that amount of an agent that, when administered to a mammal in need of such treatment, is sufficient to effect treatment for a disease mediated by TTR dissociation. Thus, a therapeutically effective amount of Compound 1 is a quantity sufficient to modulate, regulate, or inhibit the dissociation of TTR such that a disease condition that is mediated by that activity is reduced or alleviated. "Treating" is intended to mean at least the mitigation of a disease condition in a mammal, such as a human, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition. Exemplary disease conditions include senile systemic amyloidosis (SSA), familial amyloid polyneuropathy (FAP), familial amyloid cardiomyopathy (FAC), cardiac amyloidosis following liver transplantation, peripheral nerve amyloidosis following liver transplantation, leptomeningeal amyloidosis, transthyretin mutant-associated carpal tunnel syndrome, vitreous deposition, and transthyretin mutant-associated skin amyloidosis.

EXAMPLES

The examples which follow will further illustrate the preparation of the distinct forms of the invention, i.e. a crystalline form, a two-dimensionally ordered liquid crystalline form and an amorphous form, but are not intended to limit the scope of the invention as defined herein or as claimed below.

Example 1

Preparation of Crystalline Compound 1

6-Carboxy-2-(3,5-dichlorophenyl)-benzoxazole free acid (2.5 g, 8.1 mmol) and 2-propanol (49 mL) were charged to a 100 mL jacketed, 2-neck round bottom flask with magnetic stirrer. The resulting slurry was warmed to 70° C. with stirring. Water (8.8 mL) was then charged. In a separate 15 mL round bottom flask a solution of N-methyl-D-glucamine (1.58 g, 8.1 mmol) in 5 mL water was prepared and dissolved with stirring. The aqueous N-methyl-D-glucamine solution was then transferred to the reaction flask over 2 min. Most (but not all) of the solids dissolved by the end of this addition. After 5 min stirring and warming to 79° C., a clear, pale yellow solution resulted. The solution was filtered through a bed of Celite™, cooled to 60° C., then cooled to 10° C. over 2 h. The resulting solids were collected by filtration, washing with 10 mL of 2-propanol. 3.35 g product was obtained (82% yield).

Example 2

Preparation of Compound 1 Liquid Crystal

Crystalline Compound 1 (505 mg) was dissolved in 60 mL water at room temperature. The solution was transferred to a lyophilzation vessel and frozen while rotated in an acetone/dry ice bath. The vessel was transferred to a bench-top freeze dryer and allowed to dry under vacuum for approximately 19 hours, producing a white solid.

Example 3

Preparation of Amorphous Compound 1

Crystalline Compound 1 (approximately 500 mg) was transferred to an aluminum pan and placed on a 200° C. hot plate. Melting occurred within 1 minute, at which point the pan was removed from the hot plate and immediately placed in liquid nitrogen. A glassy solid resulted.

We claim:

1. A crystalline form of 6-carboxy-2-(3,5-dichlorophenyl)-benzoxazole meglumine, wherein said crystalline form has a powder X-ray diffraction pattern comprising peaks at diffraction angles (2θ) of 10.7±0.2, 11.8±0.2, and 13.3±0.2.

2. The crystalline form of 6-carboxy-2-(3,5-dichlorophenyl)-benzoxazole meglumine of claim 1, wherein said crystalline form has a powder X-ray diffraction pattern further comprising a peak at a diffraction angle (2θ) of 14.8±0.2.

3. The crystalline form of 6-carboxy-2-(3,5-dichlorophenyl)-benzoxazole meglumine of claim 1, wherein said crystalline form has a powder X-ray diffraction pattern further comprising a peak at a diffraction angle (2θ) of 21.7±0.2.

4. The crystalline form of any one of claims 1-3, wherein said form is non-hygroscopic and anhydrous.

5. The crystalline form of any one of claims 1-3, wherein said form is substantially pure.

6. A pharmaceutical composition comprising the crystalline form of any one of claims 1-3.

7. A method of treating transthyretin amyloid disease in a mammal, the method comprising administering to the mammal a therapeutically effective amount of the crystalline form of any one of claims 1-3.

8. The crystalline form of any one of claims 1-3, wherein said form comprises a plurality of small crystallites of Compound 1.

9. The crystalline form of any one of claims 1-3, wherein said form comprises a plurality of needle shaped crystals of Compound 1.

* * * * *